United States Patent [19]

Suzuma

[11] Patent Number: 5,739,685
[45] Date of Patent: Apr. 14, 1998

[54] METHOD AND APPARATUS FOR FLAW DETECTION BY LEAKAGE FLUEXES AND LEAKAGE FLUX SENSOR

[75] Inventor: Toshiyuki Suzuma, Osaka, Japan

[73] Assignee: Sumitomo Metal Industries Limited, Osaka, Japan

[21] Appl. No.: 751,693

[22] Filed: Nov. 18, 1996

Related U.S. Application Data

[62] Division of Ser. No. 549,674, filed as PCT/JP95/01254 Jun. 22, 1995.

[30] Foreign Application Priority Data

| Jun. 23, 1994 | [JP] | Japan | 6-142032 |
| May 31, 1995 | [JP] | Japan | 7-133408 |
| Jun. 5, 1995 | [JP] | Japan | 7-137798 |
| Jun. 9, 1995 | [JP] | Japan | 7-143695 |

[51] Int. Cl.$^6$ ............................. G01N 27/83
[52] U.S. Cl. ............. 324/232; 324/225; 324/235; 324/242
[58] Field of Search .............. 324/217, 219–221, 324/225, 227, 232, 235, 240–243

[56] References Cited

U.S. PATENT DOCUMENTS

| 3,535,624 | 10/1970 | Wood | 324/226 |
| 4,439,730 | 3/1984 | Kauffman | 324/232 |
| 4,477,776 | 10/1984 | Spierer | 324/232 |
| 4,495,465 | 1/1985 | Tomaiuolo et al. | 324/232 |
| 4,538,108 | 8/1985 | Huschelrath et al. | 324/232 |

FOREIGN PATENT DOCUMENTS

| 9-4629 | 12/1934 | Japan . | |
| 0042792 | 4/1977 | Japan | 324/232 |
| 57-75562 | 5/1982 | Japan . | |
| 59-22179 | 5/1984 | Japan . | |
| 1-154457 | 10/1989 | Japan . | |
| 3-33363 | 4/1991 | Japan . | |
| 4-120456 | 4/1992 | Japan . | |
| 5-60730 | 3/1993 | Japan . | |
| 1567166 | 5/1980 | United Kingdom | 324/232 |

*Primary Examiner*—Gerard R. Strecker
*Attorney, Agent, or Firm*—Burns, Doane, Swecker & Mathis, LLP

[57] ABSTRACT

A leakage flux flaw detection apparatus in which an object material is magnetized and leakage fluxes derived from a flaw are detected to thereby search for a flaw of the object material in a predetermined flaw-detection direction. The apparatus has a pair of magnet poles for magnetizing the object material in a direction different from the flaw-detection direction, another pair of magnet poles for magnetizing the object material in a direction different from the magnetization direction and flaw-detection direction of the first pair of magnet poles at a predetermined distance in the flaw-detection direction from the magnetization area of the two magnet poles, and two leakage sensors each of which is interposed between each of the two pairs of magnet poles. The leakage flux sensor which detects leakage fluxes from a flaw of the magnetized object material through two flux-sensing parts arranged in opposed relation to the object material and in predetermined spaced relation with each other along the flaw-detection direction includes two flux-sensing parts having the center distance d thereof not more than 4 mm, the length L of not less than 0.5 mm in the direction perpendicular to the flaw-detection direction, and the value d/L of nor less than 1. The leakage flux sensor includes two concentrically-arranged flux-sensing parts having circular cross sections with different cross sectional areas.

3 Claims, 44 Drawing Sheets

θ=0°
OUTPUT OF
FLUX-SENSING
PART

θ=0°
SUBTRACTION
OUTPUT

θ=45°
OUTPUT OF
FLUX-SENSING
PART

θ=45°
SUBTRACTION
OUTPUT

FIG. 35A
$\theta = 0°$
OUTPUT OF FLUX-SENSING PART
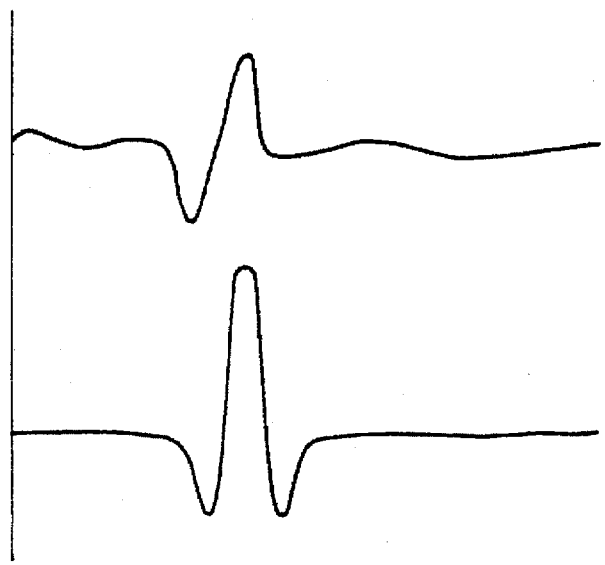
FIG. 35B
$\theta = 0°$
SUBTRACTION OUTPUT
FIG. 35C
$\theta = 45°$
OUTPUT OF FLUX-SENSING PART
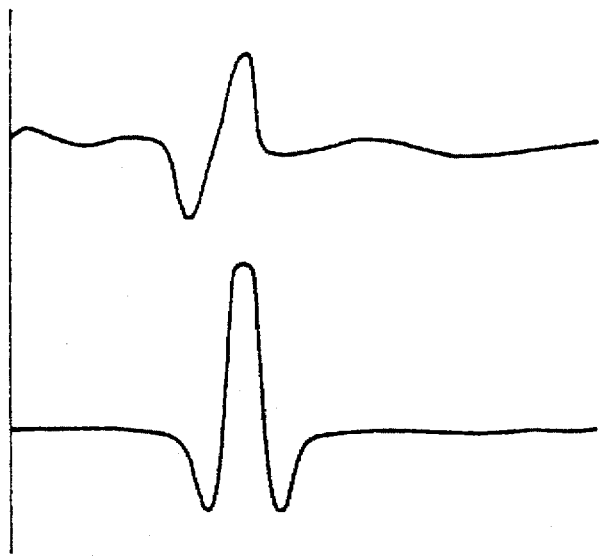
FIG. 35D
$\theta = 45°$
SUBTRACTION OUTPUT

METHOD AND APPARATUS FOR FLAW DETECTION BY LEAKAGE FLUEXES AND LEAKAGE FLUX SENSOR This application is a divisional of application Ser. No. 08/549,674, filed as PCT/JP95/01254 Jun. 22, 1995.

FIELD OF THE INVENTION

The present invention relates to a method and an apparatus for flaw detection in which an object material having magnetic properties is magnetized and leakage fluxes generated due to a flaw, which are detected to indicate a flaw of the object material, and a sensor for detecting leakage fluxes generated due to a flaw of a magnetized object material having magnetic properties.

DESCRIPTION OF RELATED ART

A method for detecting a flaw in an object material having magnetic properties by magnetizing the object material and using leakage magnetic fluxes generated due to a flaw such as a surface flaw or an internal flaw is well known.

FIG. 1 is a side view showing a model of a conventional leakage flux flaw detection apparatus of a rotary type, and FIG. 2 is a diagram showing a model partially enlarged from FIG. 1. A couple of feeders 81, 81 each including a pair of upper and lower guide rolls are arranged in predetermined spaced relationship with each other in a transportation area to hold and transport a solid-cylindrical or tubular object material P having ferromagnetic properties in the direction indicated by an arrow. The feeders 81, 81 have an annular rotary head 71 arranged therebetween in such a manner that the object material P is adapted to pass through the rotary head 71. The rotary head 71 has mounted thereon a pair of electromagnet poles 72, 72 in predetermined spaced relationship with each other along the peripheral direction of the rotary head 71 for magnetizing the object material P. A sensor 73 such as a flux-sensing element or a search coil for detecting the changes of magnetic flux density due to a flaw is mounted at substantially the center between the electromagnet poles 72,72.

The rotary head 71 is mounted coaxially with the center axis of an annular rotary unit 80 on the input side of the object material P for driving the rotary head 71. The output signal of the sensor 73 of the rotary head 71 is applied to a flaw signal analyzer 82 through the rotary unit 80. A marking unit 83 for marking the position of any flaw detected is arranged on the output side of the rotary unit 80. This marking unit 83 attaches an appropriate mark on the surface of the object material P in response to a command from the flaw signal analyzer 82.

In this apparatus, the rotary head 71 is rotated by the rotary unit 80 while the object material P is fed in the direction of the arrow by means of the feeders 81, 81. The object material P fitted in the rotary head 71 is magnetized in the peripheral direction of the object material P by electromagnet poles 72, 72, the leakage fluxes due to a flaw K are detected by a sensor 73, and the output signal of the sensor 73 is applied to the flaw signal analyzer 82. When the output signal level supplied from the sensor 73 is not less than a predetermined value, the flaw signal analyzer 82 applies a command to the marking unit 83 and causes the marking unit 83 to attach a mark along the periphery of a corresponding portion of the object material P. As a result, the object material P is searched for flaws along the whole periphery and the whole length thereof.

The conventional apparatus in which an object material is magnetized by a pair of magnet poles, however, poses the problem that the detection sensitivity is lowered in the case where the direction of a flaw occurring in the object material is approximate to the direction of magnetization of the magnet poles.

FIG. 3 is a graph showing the relation between the direction of a flaw and the sensor output. The abscissa represents an tilt angle θ with respect to the center axis of the object material, and the ordinate gives the sensor output expressed as a relative value when a flaw occurs in the direction of the center axis (i.e., θ=0°). As seen from FIG. 3, the sensor output is strongest when the flaw lies in the direction of the center axis of the object material (θ=0°), and steadily decreases with the increase in the angle θ. When the angle θ reaches the direction perpendicular to the center axis, i.e., the magnetization direction, the sensor output substantially disappears in spite of a flaw which may exist.

In view of the above-mentioned fact, an apparatus is proposed as disclosed in Japanese Patent Application Publication No. 59-22179. In this apparatus, two pairs of magnetic poles are arranged in cross in opposed relation with a tabular object material, with each magnetic pole being connected to an AC power supply. A sensor is provided at each crossing point of the two pairs of magnetic poles. The two pairs of magnetic poles are excited by AC currents different in phase by $\pi/2$ supplied from an AC power supply. A rotary magnetic field directed clockwise or counterclockwise is thus formed, and the leakage fluxes due to a flaw are detected by the sensor located at the center of rotation. As a result, flaws positioned in any direction can be detected with high sensitivity.

In the above-mentioned conventional apparatus, however, a flaw is searched by using a rotary magnetic field generated by application of an AC current. An internal flaw of an object material or a flaw in the internal surface of a tubular object material, therefore, cannot be successfully detected. Also, since the rotary magnetic field changes in direction with time, it is difficult to detect the direction and depth of a flaw quantitatively. These problems may be obviated by magnetization using DC current (DC magnetization). In view of the fact that two pairs of magnetic poles are arranged in cross, however, simultaneous DC magnetization by the two pairs of magnetic poles is impossible. Another related problem is that alternate DC magnetizations will decrease the flaw detection speed.

The sensor 73 used for detecting leakage fluxes in the above-mentioned leakage flux flaw detection apparatus normally includes a magnetic sensor made of a flux-sensing element such as a Hall probe or a magnetoresistive element, or a coil sensor wound on a ferrite core.

Generally, the conventional sensor 73 is such that in order to increase the detection sensitivity thereof with respect to a linear flaw K occurring often in the longitudinal direction of the object material P, the cross section of the flux-sensing pars is formed in rectangular shape, and the apparatus is arranged in such a manner that the longitudinal side of the rectangle is parallel to the direction in which a flaw K extends. The flaw K has a length of 8 mm to 14 mm and is often such a serious flaw as to reduce the product quality. In the sensor 73 having a single flux-sensing part, the noises caused by the vibrations due to the transportation of the object material P or the rotational drive of the rotary head 71 cannot be reduced, resulting in a low S/N ratio. For this reason, a sensor having two flux-sensing parts described below has been realized in practical applications.

FIG. 4 is a plan view showing a model of a conventional sensor for detecting leakage fluxes. A sensor 76 includes two flux-sensing parts 75, 75 in opposed relation to each other. The flux-sensing parts 75, 75 are arranged in predetermined spaced relationship with each other along the flaw-detection direction indicated by a white arrow in the drawing. The flux-sensing parts 75, 75 are quadrilateral in shape with longitudinal sides thereof lying in the direction perpendicular to the flaw-detection direction, and have a length L of about 3 mm. Also, the distance d between the centers $O_1$ and $O_2$ of the two flux-sensing parts 75, 75 is about 1 mm.

FIG. 5 is a plan view showing the manner in which the sensor 76 shown in FIG. 4 searches for a flaw. FIG. 6 is a side sectional view showing the same situation as FIG. 5. A flaw K often occurs in the longitudinal direction of the object material P. In order to detect such a flaw K with high sensitivity, the sensor 76 searches for a flaw of the object material P in the direction perpendicular to the longitudinal direction thereof as indicated by a white arrow in FIG. 4 with the flux-sensing parts 75, 75 arranged in parallel to the longitudinal direction of the object material P.

The object material P is magnetized in a direction different from the flaw-detection direction by the sensor 76, so that as shown in FIG. 6, a magnetic flux J in the vicinity of the flaw K leaks upward of the flaw K from the object material P and returns to the object material P again. As a consequence, when the flux-sensing parts 75, 75 of the sensor 76 come to positions on either side of the flaw K, the flux-sensing parts 75, 75 detect magnetic fluxes of opposite polarities to each other. The resulting detection signals of the flux-sensing parts 75, 75 are subtracted from each other thereby to amplify the flaw signal. The noise generated by vibrations due to the transportation of the object material P or the scanning of the sensor 76, on the other hand, is detected as the same polarity by the flux-sensing parts 75, 75. The noise signal detected, therefore, is reduced in level by the above-mentioned differential operation, thereby leading to a high S/N ratio.

FIGS. 7A-7C are graphs showing the detection signals of the flux-sensing parts 75, 75 of the sensor 76 in FIG. 6 and the detection signals subjected to the differential operation.

FIG. 7(a) represents a detection signal of a flux-sensing part 75 positioned ahead in the flaw-detection direction, and FIG. 7(b) represents a detection signal of a flux-sensing part 75 behind the flaw-detection direction, and FIG. 7(c) represents a signal subjected to the differential operation. As seen from FIGS. 7(a) and (b), the flux-sensing part 75 positioned ahead in the flaw-detection direction detects an upward flaw signal following a downward flaw signal. The flux-sensing part 75 in the behind position detects a downward flaw signal at the timing of detection of the upward flaw signal. On the other hand, an unevenness due to the noise signal is generated in the base line of the detection signal of each of the flux-sensing parts 75, 75. The directions of the unevennesses, however, are identical as seen from FIG. 7(a) and FIG. 7(b). As a result, as seen from FIG. 7(c), when the detection signals of the flux-sensing parts 75, 75 are subjected to the differential operation, the flaw signal is amplified to a large amplitude, and the noise signal is reduced with the base line substantially assuming a linear form. Thus the S/N ratio is increased and the flaw detection sensitivity is improved.

The conventional leakage flux sensor described above has the following problem. FIG. 8 is a plan view showing the relationship between a sensor having two flux-sensing parts and a tilted flaw. In FIG. 8, numeral 76 designates a sensor. The sensor 76 for searching for a flaw of the object material P in the direction of the white arrow, as described above, includes flux-sensing parts 75, 75 in the direction perpendicular to the flaw-detection direction. Assuming that a flaw K1 in parallel to the flux-sensing parts 75, 75 is set as a reference, a flaw K2 indicated by the dashed line is inclined by θ from the direction of the reference flaw K1. Assuming that this θ is the tilt angle, generally, the amplitude of the flaw signal detected by the flux-sensing parts 75, 75 is at a local maximum when the tilt angle θ is 0° and decreases with the increase in the tilt angle θ from 0°.

FIG. 9 is a graph showing the relation between the tilt angle θ of a flaw and the amplitude of a flaw signal in the conventional leakage flux sensor. In this graph, the ordinate represents the amplitude of the flaw signal, and the abscissa the tilt angle θ. As seen from FIG. 9, in the conventional leakage flux sensor, the amplitude of the flaw signal assumes a local maximum when the tilt angle θ is 0° and continues to assume substantially the same level until the tilt angle θ reaches about 18°. Beyond this angle, the amplitude of the flaw signal is sharply reduced. In this case, a tilt angle θ (of about 18°) is a critical tilt angle.

As shown in FIG. 10, in the conventional leakage flux sensor, the length L of the flux-sensing parts 75, 75 is 3 mm and the distance d is 1 mm. The angle $θ_c$ (critical tilt angle) formed between a line segment connecting the center of an end of a flux-sensing part 75 and the center of the other end of the other flux-sensing part 75 on the one hand and the center axis $u_1(u_2)$ in the longitudinal direction of the flux-sensing part 75 (75) on the other hand is about 18°. As a result, the flaw K having an tilt angle θ of about 18° or more is such that the flaw signal thereof is detected simultaneously by the flux-sensing parts 75, 75 and therefore the amplitude of the flaw signal is reduced by the differential operation.

In this way, in the conventional leakage flux sensor, the critical tilt angle $θ_c$ is so small that it is easily exceeded even for a flaw with a comparatively small tilt angle θ. Thus the amplitude of the flaw detection signal is so small as to cause an erroneous decision.

Even in the case where there exists a flaw having an tilt angle θ with respect to the reference direction (center axis of the object material), it is thought that such a flaw can be detected with high sensitivity by the following method. According to this method, as shown in FIG. 11, a single flux-sensing part 80 having a circular cross section is scanned in the direction perpendicular to the reference direction. In this case, as shown in FIGS. 12(A) and 12(B), regardless of the tilt angle θ of the flaw K, the relative positions of the flux-sensing part 80 and the flaw K in the same plane are fixed around the axis of the flux-sensing part 80, and therefore the output of the flux-sensing part 80 remains constant. As a result, the linear flaw K can be detected with high sensitivity without being affected by the tilt angle θ. In the case of using a differential-type sensor having two such flux-sensing parts 80 arranged in parallel in the scanning direction and connected to each other differentially in order to introduce a differential operation effective for noise signal suppression, however, the same phenomenon occurs as the two flux-sensing parts 75 having a rectangular cross section are arranged in parallel as described above. Therefore, an actual flaw inclined in a direction different from the reference direction cannot be detected with the same sensitivity as a flaw extending in the reference direction.

An object of the invention is to provide a method and an apparatus for flaw detection by leakage fluxes in which a flaw can be magnetized by DC current in a different direction without reducing the flaw-detection speed.

Another object of the invention is to provide a method and an apparatus for flaw detection by leakage fluxes in which the tilt angle and depth of a flaw can be detected quantitatively.

A further object of the invention is to provide a method and an apparatus for flaw detection by leakage fluxes in which the leakage fluxes from a flaw can be increased, thereby making it possible to detect a flaw with high sensitivity.

A still further object of the invention is to provide a leakage flux sensor in which the critical tilt angle can be increased and even a flaw with a comparatively large tilt angle can be detected with high sensitivity.

A yet further object of the invention is to provide a leakage flux sensor which can be used as a differential-type sensor employing an effective differential operation low in cost and simple as a noise suppression means, and in which even an actual flaw tilted in a direction other than the reference direction can be detected with a high accuracy and with a predetermined sensitivity as far as the depth of the flaw remains the same.

SUMMARY OF THE INVENTION

An apparatus for flaw detection by leakage fluxes according to the present invention for magnetizing an object material with a pair of magnet poles, detecting leakage fluxes with a sensor arranged between the pair of magnet poles and at the same time searching for a flaw of the object material in a predetermined direction, has a pair of magnet poles for magnetizing the object material in a direction different from the flaw-detection direction, another pair of magnet poles arranged in predetermined spaced relation with the magnetization areas of the two magnet poles in the flaw-detection direction for magnetizing the object material in a direction different from the magnetization direction and the flaw-detection direction, and a plurality of sensors each arranged between each pair of the magnet poles. The two pairs of magnet poles with the magnetization areas thereof arranged in predetermined spaced relation with each other in the flaw-detection direction are used for magnetizing the object material in different directions from each other with respect to the flaw-detection direction. As a result, a flaw which may occur, in whichever direction it is located in the object material, crosses one of the magnetization directions and therefore generates leakage fluxes. The leakage fluxes thus generated are detected by either of the sensors arranged between each pair of the magnet poles. Since the two pairs of magnet poles have the magnetization areas thereof arranged in spaced relation to each other, DC magnetization is possible thereby to detect the direction and depth of a flaw quantitatively.

In the above-mentioned apparatus for flaw detection by leakage fluxes, the magnetization direction of the two pairs of magnet poles can be changed, and the two sensors have the detection areas thereof changeable. As a result, the direction in which the object material is magnetized is adjusted to the tilt angle of a frequently-occurring flaw by changing the position of one of the magnet poles constituting each magnet pair or by changing the distance between the two magnet poles. This also can increase the leakage fluxes from a flaw. The detection area of the sensors, which can be changed appropriately, is adjusted in accordance with the adjustment of the magnetization direction.

In another apparatus for flaw detection by leakage fluxes according to the invention, a tubular material is magnetized by a pair of magnet poles, and leakage fluxes are detected by a sensor arranged between the two magnet poles while a flaw of the tubular material is searched for in the peripheral direction. The two magnet poles are arranged in such a manner as to form two magnetization areas along the peripheral surface of the tubular material in directions different from the peripheral direction, with two sensors each of which is provided in each of the two magnetization areas. The tubular material is magnetized in two directions different from the peripheral direction providing the flaw-detection direction by a pair of magnet poles. As a consequence, any flaw which may occur in the tubular material, regardless of the direction in which it is located, crosses one of the magnetization directions, and therefore, leakage fluxes are generated. The leakage fluxes thus generated are detected by the sensors arranged in the two magnetization areas. A tubular material can be DC magnetized in two directions by a pair of magnet poles, whereby the direction and depth of a flaw can be detected quantitatively.

In the above-mentioned apparatus for flaw detection by leakage fluxes, the magnetization direction of the two magnet poles is changeable, and the two sensors have the detection areas thereof also changeable. As a result, the direction in which the tubular material is magnetized is adjusted to the tilt angle of a frequently-occurring flaw by changing the position of one of the two magnet poles or by changing the distance between the two magnet poles. The leakage fluxes from the flaw thus can be increased. Also, the detection area of the sensors, which is changeable, is appropriately adjusted in accordance with the adjustment of the magnetization direction.

Still another apparatus for flaw detection by leakage fluxes according to the invention has, in addition to the above-mentioned configuration, means for calculating the output ratio between the two sensors, means for determining the tilt angle of the target flaw on the basis of the predetermined relation between the output ratio and the flaw tilt angle and the calculated output ratio, means for correcting the amplitude of the output signals of the two sensors on the basis of the predetermined relation between the flaw tilt angle and the amplitude change rate of the sensor output signal and the tilt angle of the target flaw determined, and means for calculating the depth of the target flaw on the basis of the corrected amplitude of the output signal.

A leakage flux sensor according to the invention is arranged in opposed relation to an object material for detecting leakage fluxes generated in a flaw of a magnetized object material by means of two flux-sensing parts provided in predetermined spaced relationship with each other in the flaw-detection direction. The two flux-sensing parts are not more than 4 mm in the distance d between the centers thereof, with the length L of not less than 0.5 mm in the direction perpendicular to the flaw-detection direction, and d/L not less than 1. As far as the center distance d of the two flux-sensing parts is in the range of not more than 4 mm, the detection signal is amplified and a flaw can be detected with high sensitivity by subtracting the detection signals produced from the two flux-sensing parts. The length L of the flux-sensing parts in the direction perpendicular to the flaw-detection direction can be reduced to a minimum of 0.5 mm. When d/L is not less than 1, the critical tilt angle $\theta_c$ is approximately 45° even when the length L is 0.5 mm, so that even a flaw with a comparatively large tilt angle $\theta$ can be detected with high sensitivity.

In the above-mentioned leakage flux sensor, assume that the portion of the two flux-sensing parts in opposed relation with the object material is substantially a circle or a regular polygon in shape. Regardless of the flaw tilt angle, the levels of the detection signals of the two flux-sensing parts are substantially the same.

Still another leakage flux sensor according to the invention is a sensor for detecting magnetic fluxes leaking from a flaw of an object material magnetized, and is so configured that the cross section thereof is formed in circle and two flux-sensing parts having different cross sectional areas are arranged concentrically. The concentrical arrangement of two flux-sensing parts with circular cross sections having different cross sectional areas contributes to maintaining a constant relative position between the two flux-sensing parts and a flaw in a horizontal plane around the axis thereof even in the case of detecting magnetic fluxes leaking from an actual flaw tilted in a direction other than the reference direction. As a consequence, the outputs of the flux-sensing parts are always constant and are not affected by the tilt angle of the flaw. It is thus possible to detect with high accuracy even an actual flaw tilted in a direction other than the reference direction.

BRIEF DESCRIPTION OF THE DRAWINGS

FIGS. 35A–35D are diagrams showing waveforms of detection signals from a leakage flux sensor according to a first embodiment and signals obtained by differential operation between the two detection signals.

DESCRIPTION OF THE PREFERRED EMBODIMENTS

The present invention will be specifically explained below with reference to the drawings showing embodiments thereof.

(Leakage flux flaw detection apparatus)

Figure 13:
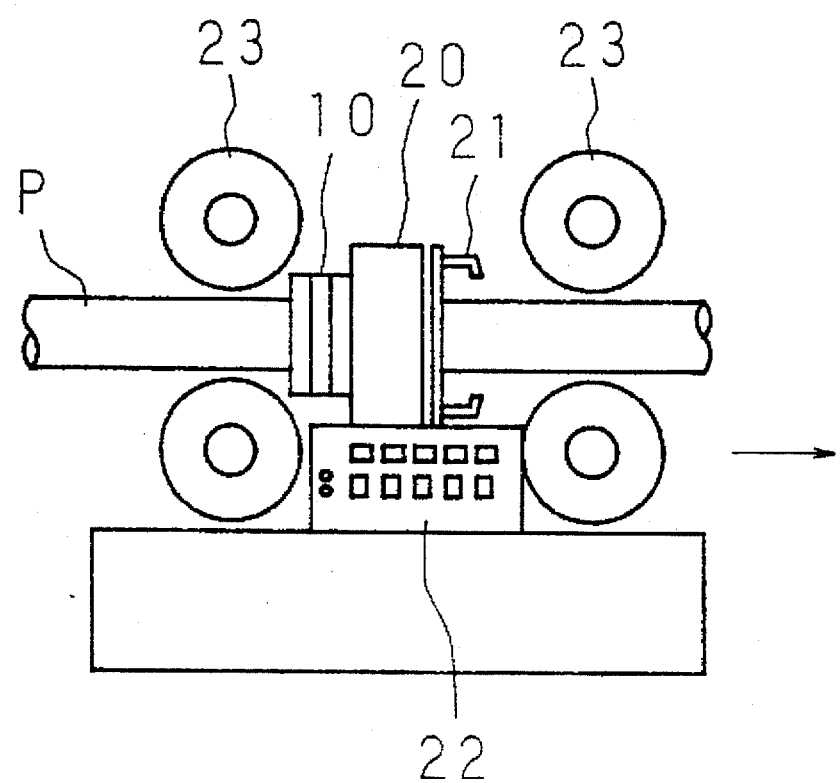
FIG. 13 is a side view schematically showing a leakage flux flaw detection apparatus according to the invention.

FIG. 13 is a side view schematically showing a leakage flux flaw detection apparatus according to the invention. In FIG. 13, P designates a solid-cylindrical or a tubular object material having ferromagnetic properties. A pair of feeders 23, 23 each having a pair of upper and lower guide rolls for holding and transporting the object material P in the direction indicated by an arrow are arranged in predetermined spaced relationship in the transportation range of the object material P. The feeders 23, 23 have, interposed therebetween, an annular rotary head 10 with a plurality of electromagnet poles for magnetizing the object material P and a sensor for detecting leakage fluxes. The object material P is adapted to pass through the rotary head 10.

The rotary head 10 is mounted coaxially with the center axis of an annular rotary unit 20 on the input side thereof for rotating the rotary head 10. A flaw of the object material P is searched for over the enter periphery and the entire length thereof while being transported through the rotary head 10 in rotation by feeders 23, 23. The output signal from the sensor of the rotary head 10 is applied to a flaw signal analyzer 22 through the rotary unit 20. A marking unit 21 for marking the position of a detected flaw is arranged on the output side of the rotary unit 20. In the case where it is decided that a flaw exists, the flaw signal analyzer 22 applies a command to the marking unit 21 to mark around a corresponding portion of the object material P.

Figure 14:
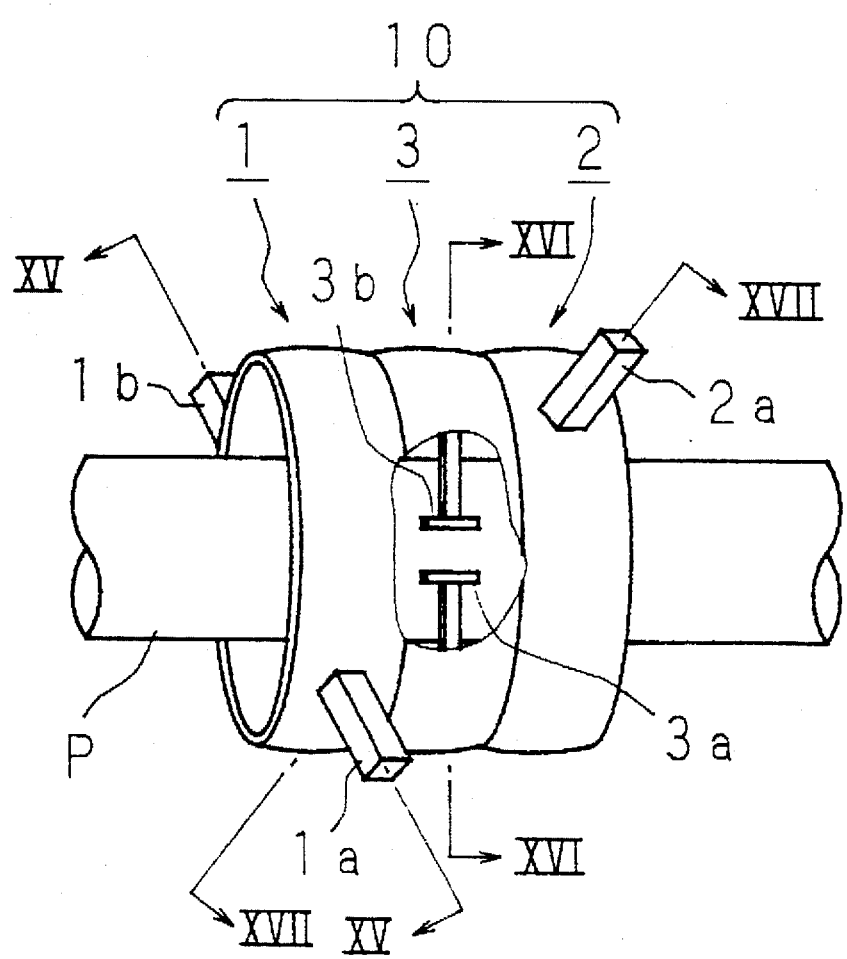
FIG. 14 is a partially cutaway perspective view of a rotary head shown in FIG. 13.
Figure 15:
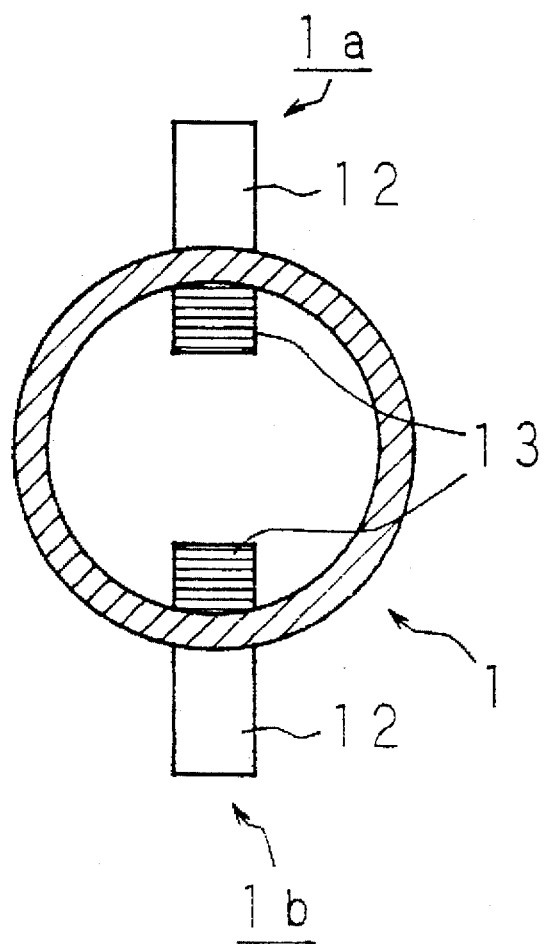
FIG. 15 is a sectional view taken in line XV—XV in FIG. 14.
Figure 16:
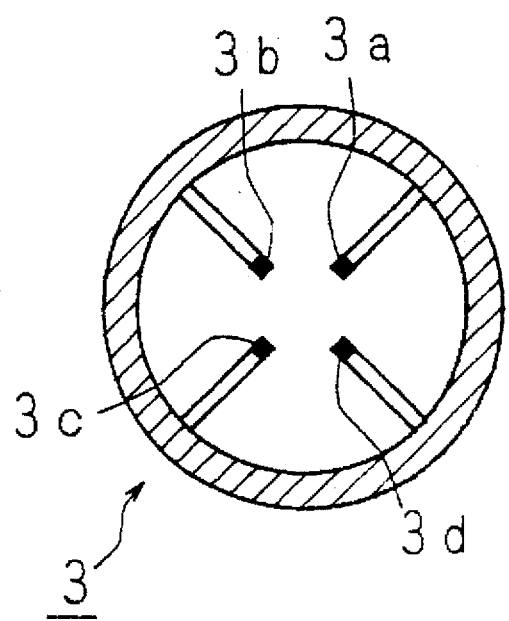
FIG. 16 is a sectional view taken in line XVI—XVI in FIG. 14.
Figure 17:
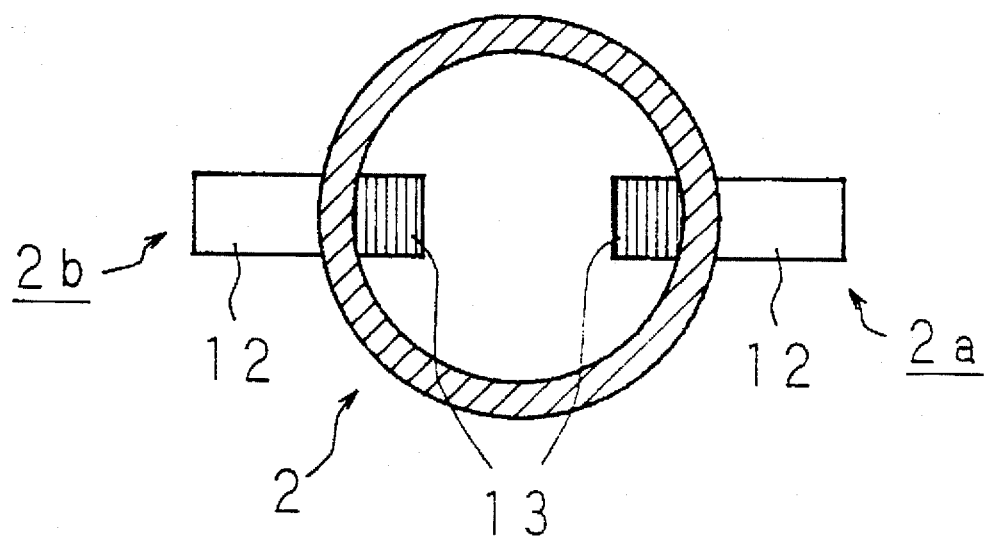
FIG. 17 is a sectional view taken in line XVII—XVII in FIG. 14.

FIG. 14 is a partially cutaway perspective view of the rotary head 10 shown in FIG. 13. FIGS. 15, 16 and 17 are a sectional view taken in line XV—XV, a sectional view taken in line XVI—XVI, and a sectional view taken in line XVII—XVII respectively in FIG. 14. The rotary head 10, as shown in FIGS. 14 and 16, includes a first magnetic pole unit 1 having two electromagnet poles 1a, 1b mounted in opposed relation thereon, a detector 3 having four sensors 3a, 3b, 3c, 3d such as a flux-sensing element or a search coil mounted thereon for detecting leakage fluxes, and a second magnetic pole unit 2 having two electromagnet poles 2a, 2b mounted in opposed relation in the direction substantially perpendicular to the direction of the electromagnet poles 1a, 1b of the first magnetic pole 1, respectively. The sensors 3a, 3b, 3c, 3d are arranged at substantially the mid-point of a line connecting the electromagnet poles 1a, 1b of the first magnetic pole 1 and the electromagnet poles 2a, 2b of the second magnetic pole 2.

Each of the electromagnet poles 1a, 1b, 2a, 2b of the first magnetic pole unit 1 and the second magnetic pole unit 2, as shown in FIGS. 15 and 17, have the cores 12, 12, 12, 12 thereof protruding into the rotary head 10 by a predetermined length, and magnetizing coils 13, 13, 13, 13 are wound on the protrusion. The two electromagnet poles 1a, 1b of the first magnetic pole unit 1 are excited to be N pole (S pole), while the electromagnet poles 2a, 2b of the second magnetic pole unit 2 are excited in the reverse polarity. As a result, the object material P is magnetized in four directions at symmetric angles diagonal to the center axis thereof.

Although according to the embodiment under consideration, each pair of the first electromagnet poles 1a, 1b and the second electromagnet poles 2a, 2b are mounted on the first magnetic pole unit 1 and the second magnetic pole unit 2 respectively, it is sufficient if one magnet pole is mounted on at least selected one of the first magnetic pole unit 1 and the second magnetic pole unit 2 with two magnet poles being mounted in polarities opposite to the magnet pole on the other magnetic pole. Also, in spite of the electromagnet poles being mounted on the rotary head 10 for searching a solid-cylindrical or a tubular material according to the present embodiment, a configuration for searching a tabular material is applicable with equal effect.

Figure 18:
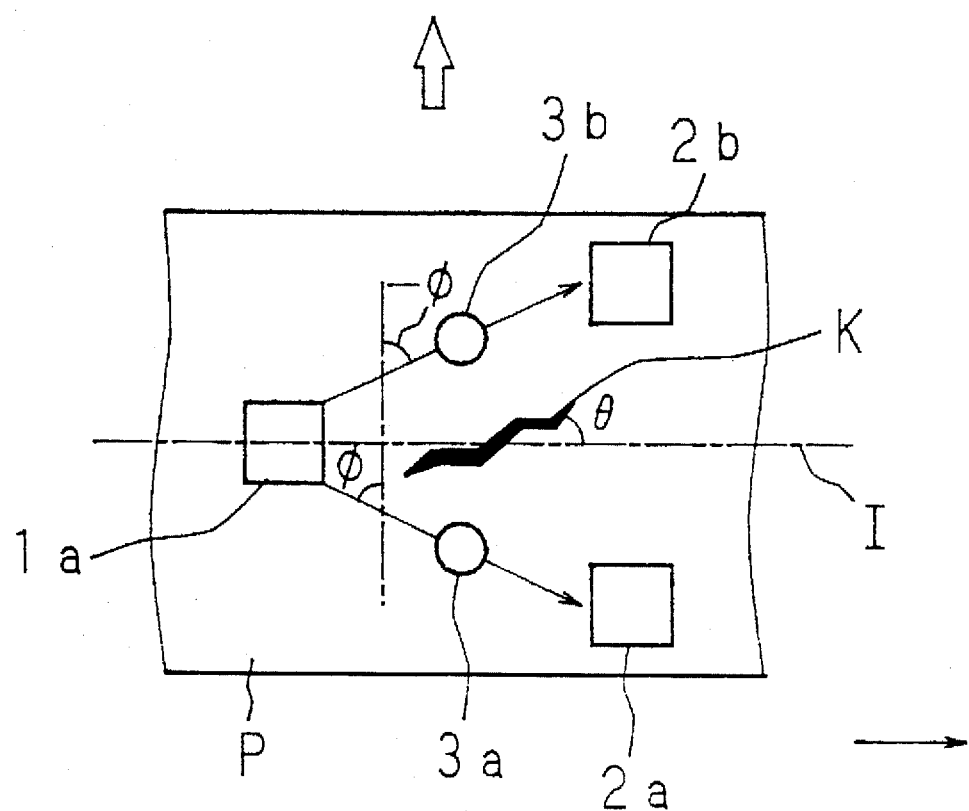
FIG. 18 is a plan view schematically showing important parts of a leakage flux flaw detection apparatus according to the invention.

FIG. 18 is a plan view schematically showing important parts of a leakage flux flaw detection apparatus according to the invention. An electromagnet pole 1a of a first magnetic pole is arranged upstream of an object material P transported in the direction indicated by an arrow, and an electromagnet poles 2a, 2b of a second magnetic pole downstream in opposed relation with the center axis I of the object material P in between. A first sensor 3a and a second sensor 3b are arranged at substantially the mid point between one of the first electromagnet poles 1a of the first magnetic pole unit 1 and the second electromagnet poles 2a, 2b of the second magnetic pole unit 2.

The electromagnet pole 1a of the first magnetic pole unit 1 is excited to N polarity, and the electromagnet poles 2a, 2b of the second magnetic pole unit 2 to S polarity, for example. Consequently, there arise a magnetization area of magnetization angle $\phi$ in plan view with respect to the axis perpendicular to the center axis I of the object material P and a magnetization area of magnetization angle $-\phi$ symmetric with the first magnetization area with respect to the center axis from the electromagnet pole 1a of the first magnetic pole to the electromagnet poles 2a, 2b of the second magnetic pole. The flaw-detecTion operation is performed in the direction of the white arrow so that a flaw K with a tilt angle of $\theta$ with respect to the center axis I of the object material P is magnetized by the above-mentioned magnetization areas respectively, and the leakage fluxes thereof are detected by the two sensors 3a, 3b.

The rotary head 10 shown in FIG. 14 have a spacer interposed between the detector 3 and the first magnetic pole 1 and also between the detector 3 and the second magnetic pole 2, respectively. The spacer is prepared in a variety of widths, whereby the magnetization angle ($\phi$, $-\phi$) can be changed appropriately. A high detection sensitivity can be maintained by changing the magnetization angle ($\phi$, $-\phi$) to a frequently-occurring value of tilt angle $\theta$ at predetermined time intervals.

Figure 19:
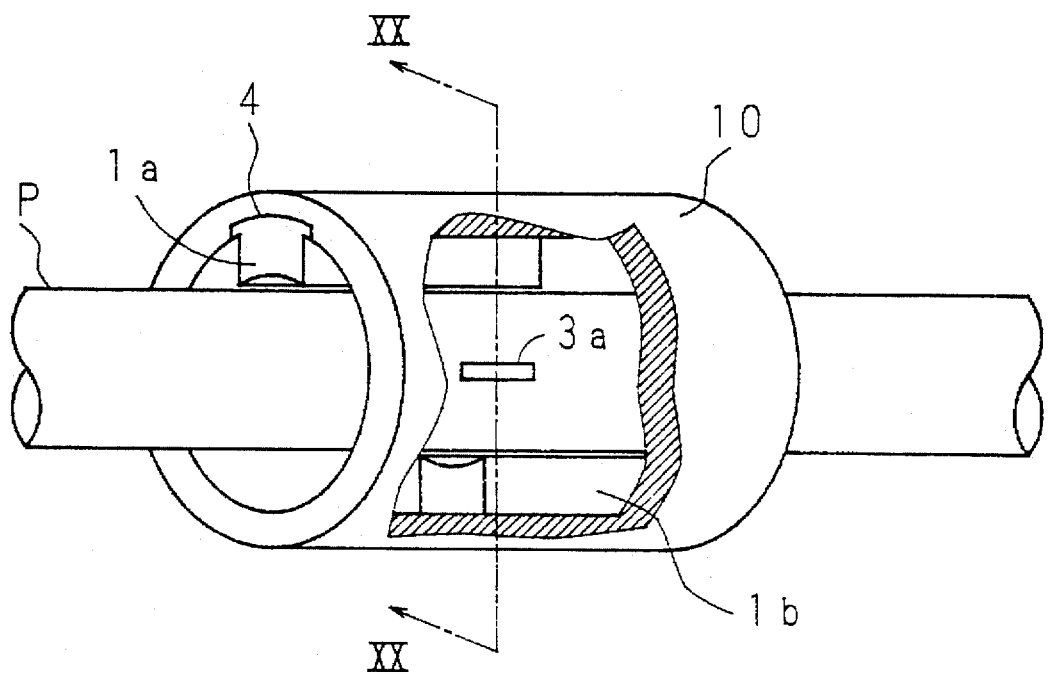
FIG. 19 is a partially cutaway perspective view showing important parts of a leakage flux flaw detection apparatus according to another embodiment of the invention.
Figure 20:
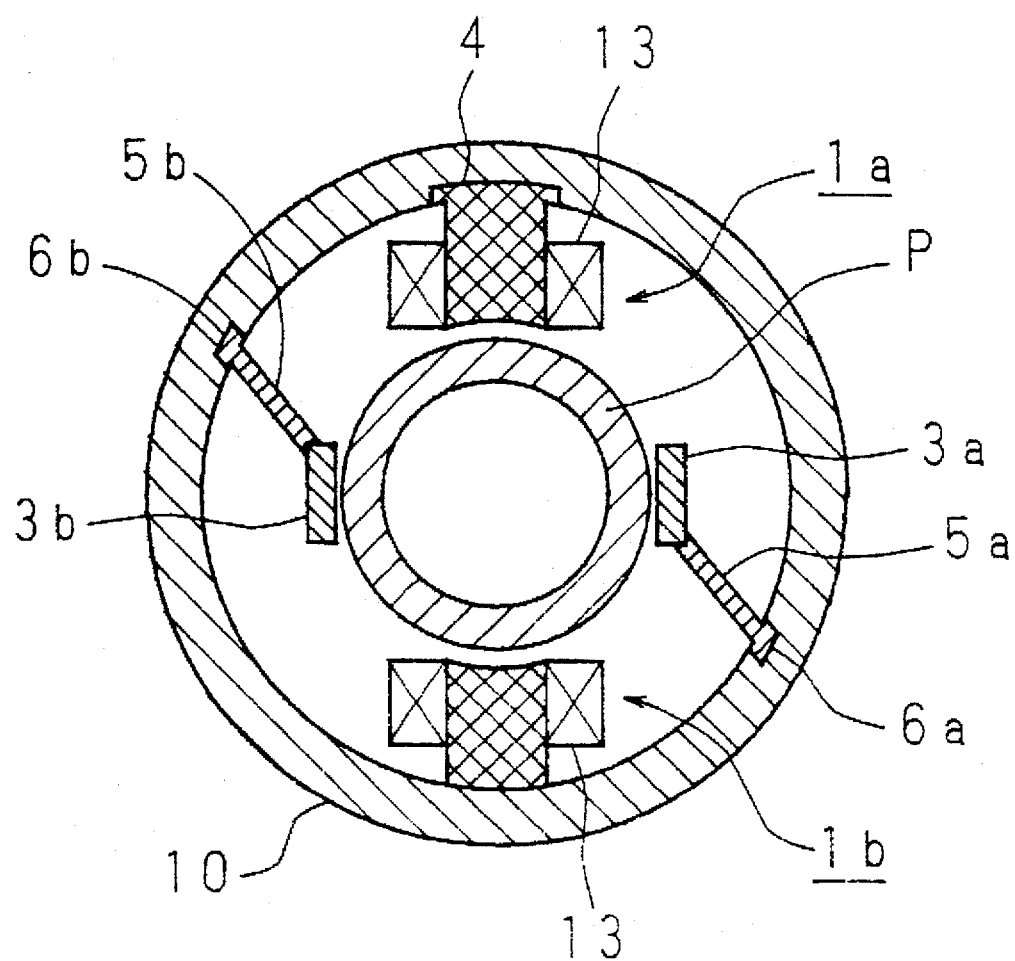
FIG. 20 is a sectional view taken in line XX—XX in FIG. 19.

FIG. 19 is a partially cutaway perspective view showing a leakage flux flaw detection apparatus according to another embodiment of the invention. A pair of electromagnet poles 1a, 1b are used to magnetize the object material P in two directions different from the flaw-detection direction. FIG. 20 is a sectional view taken in line XX—XX in FIG. 19. A groove 4 is formed longitudinally in the inner peripheral wall of a hollow-cylindrical rotary head 10. An electromagnet pole 1a is slidable fitted and fixed at an end of the groove 4. Also, an electromagnet pole 1b is fixed at a position turned by about 180° with respect to the electromagnet pole 1a in the inner peripheral wall of the other end of the rotary head 10. In this way, the object material P is magnetized by the electromagnet poles 1a, 1b in two directions passing through the peripheral surface of the object material P connecting the centers of the electromagnet poles 1a, 1b. Also, the above-mentioned magnetization angle (φ, −φ) can be changed by changing the position of the electromagnet pole 1a. As a result, as in the aforementioned embodiment, a high detection sensitivity can be maintained by changing the magnetization angle (φ, −φ) to a frequently-occurring tilt angle θ.

Other grooves 6a, 6b are formed in the inner peripheral wall between the two electromagnet poles 1a, 1b of the rotary head 10, and support rods 5a, 5b for supporting the sensors 3a, 3b are slidable fitted and fixed at the forward end of the grooves 6a, 6b, respectively. The position of the support rods 5a, 5b is adjusted so that the sensors 3a, 3b supported by the support rods 5a, 5b are positioned above the mid point of two line segments connecting the centers of the two electromagnet poles 1a, 1b and passing through the peripheral surface of the object material P. As a result, even when the position of the electromagnet pole 1a is changed, the sensors 3a, 3b are capable of detecting leakage fluxes from a flaw with high sensitivity. Although according to this embodiment the position of the electromagnet pole 1a is changeable, an arrangement may of course be made so that the position of the electromagnet pole 1b may also be changeable.

Figure 21:
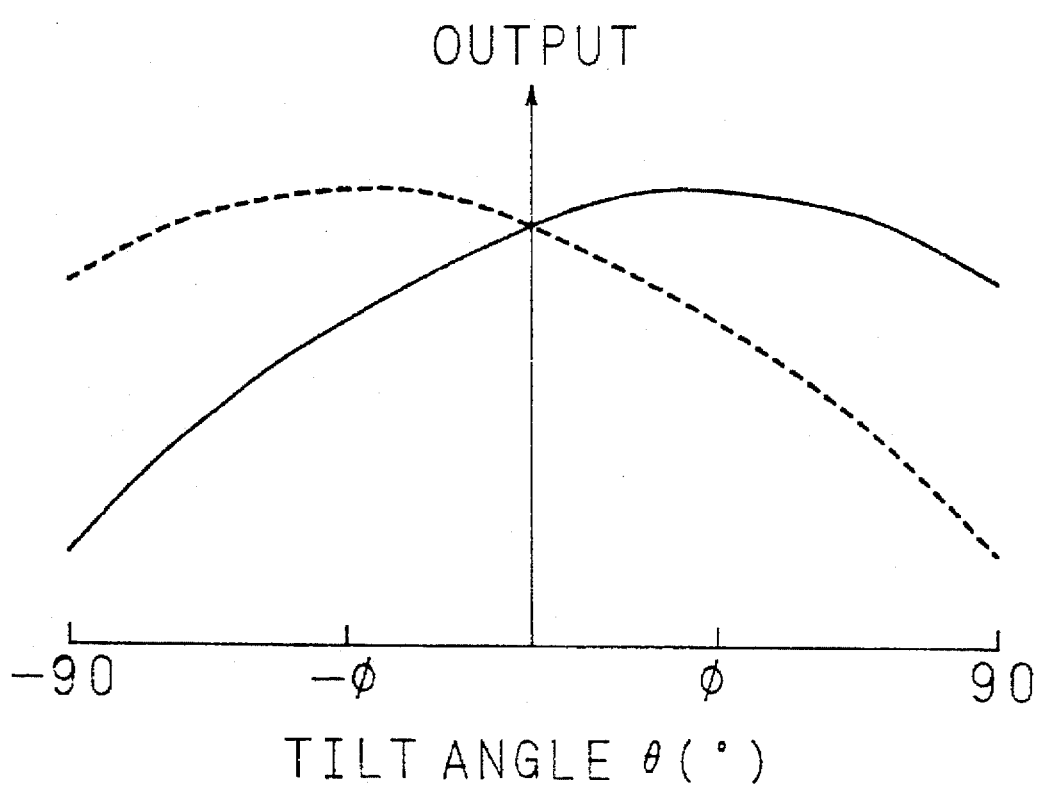
FIG. 21 is a graph showing the relation between the flaw tilt angle and the outputs of the two sensors.

FIG. 21 is a graph showing the relation between the flaw tilt angle and the sensor output of a leakage flux flaw detection apparatus according to the invention. In this graph, a solid line represents the output (amplitude) of a sensor (first sensor) described above, and a dashed line the output (amplitude) of the other sensor (second sensor). As seen from FIG. 21, the outputs of the two sensors both undergo a change in accordance with the flaw tilt angle. The changes of the two outputs are symmetric with each other. The output of the first sensor assumes a local maximum when the flaw tilt angle θ with respect to an axis orthogonal to the flaw-detection direction is φ, while the output of the second sensor takes a local maximum value when the tilt angle θ is −φ. The output ratio of the two sensors is determined as described below.

Figure 22:
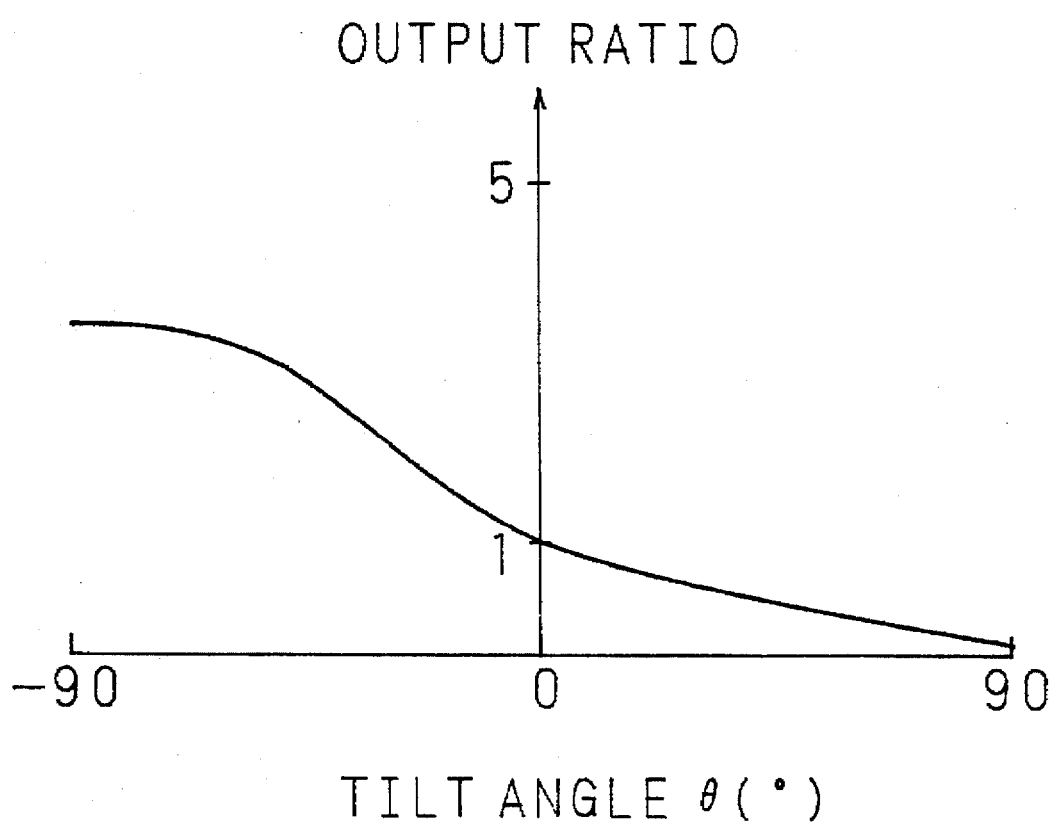
FIG. 22 is a graph showing the relation between the flaw tilt angle and the output ratio of the two sensors.

FIG. 22 is a graph showing the output ratio between the first and second sensors. As shown in FIG. 22, the output ratio between the first and second sensors forms a sigmoid curve passing through a point 1 in the case where the tilt angle θ is 0, that is, a flaw is located in the direction perpendicular to the flaw-detection direction, and the output ratio and the tilt angle θ are in one-to-one correspondence to each other in accordance with this curve. This curve thus can be used as a verification curve. In this way, the tilt angle θ of a flaw can be calculated on the basis of the detected output ratio between the first sensor and the second sensor by determining such a verification curve in advance.

Once the tilt angle θ of a flaw is calculated, the amplitude of the sensor output signal can be corrected based on the graph of FIG. 21. The corrected amplitude of the output signal is directly proportional to the flaw depth, and therefore the flaw depth can be determined by determining the relationship between the two factors in advance by a test using an artificial flaw of a known depth.

Figure 23:
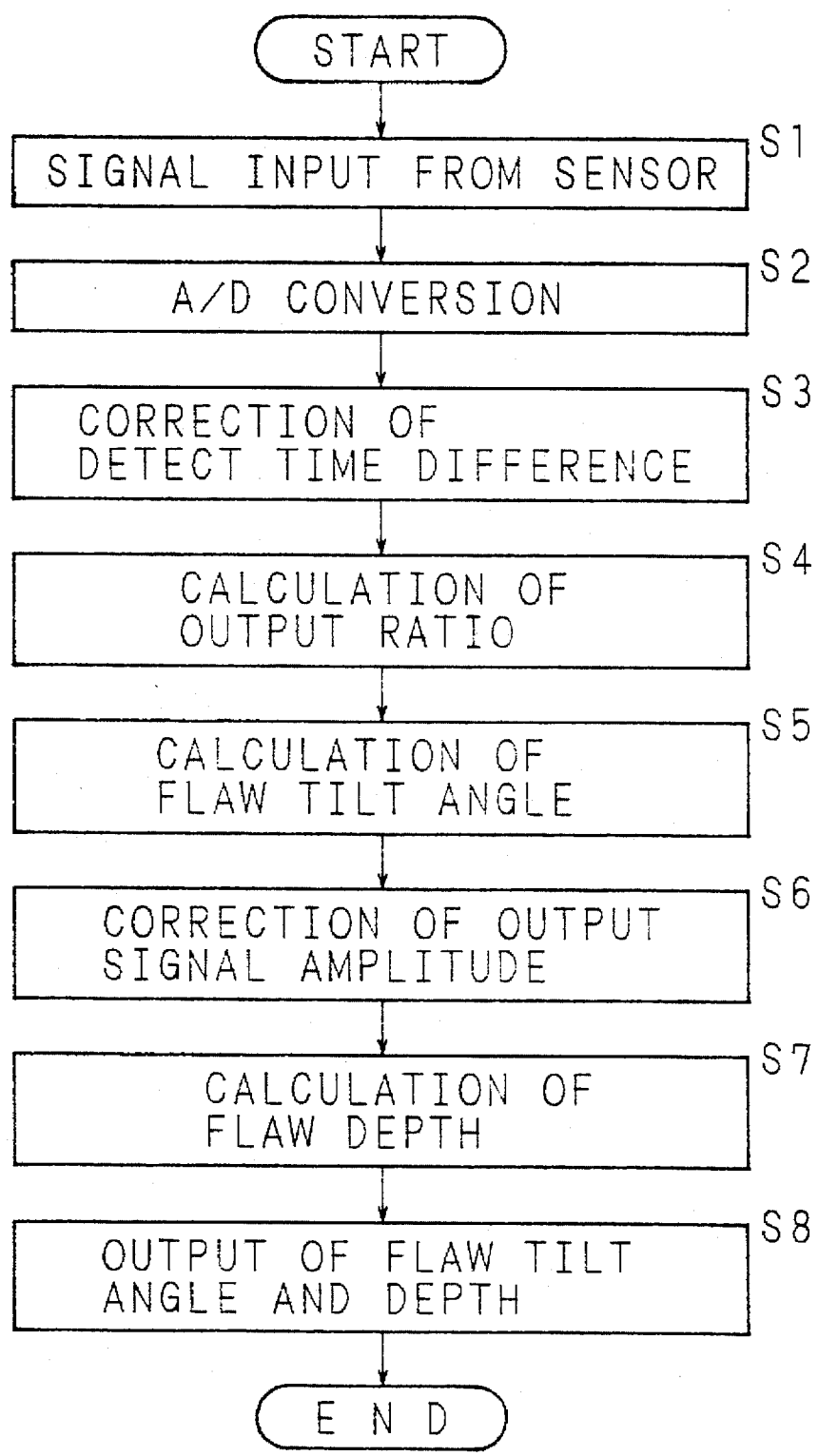
FIG. 23 is a flowchart showing the order of processes in a leakage flux flaw detection method according to the invention.

FIG. 23 is a flowchart showing the sequence of steps for processing the output signals of the first sensor 3a and the second sensor 3b shown in FIG. 18. The output signals of the first sensor 3a and the second sensor 3b are fetched (step S1) and are converted into digital signals (step S2). The time difference of detection between the first sensor 3a and the second sensor 3b for the same flaw is corrected (step S3), followed by calculating the output ratio between the two sensors (step S4).

The tilt angle of a target flaw is determined (step S5) on the basis of the relation between a predetermined flaw tilt angle and the output ratio (FIG. 22) on the one hand and the output ratio calculated at step S4 on the other hand. In similar fashion, the amplitude of the output signals of the first sensor 3a and the second sensor 3b is corrected (step S6) on the basis of the relation between a predetermined flaw tilt angle and the change in the output signal amplitude (FIG. 21) on the one hand and the tilt angle of the target flaw determined at step S5 on the other hand. Also, the depth of the target flaw is calculated on the basis of the relation between a predetermined amplitude of the output signal and the flaw depth on the one hand and the corrected amplitude of the output signal on the other hand (step S7). Then the tilt angle of the target flaw determined at step S5 and the flaw depth determined at step S7 are applied to an external memory unit or the like (step S8).

Figure 24A:
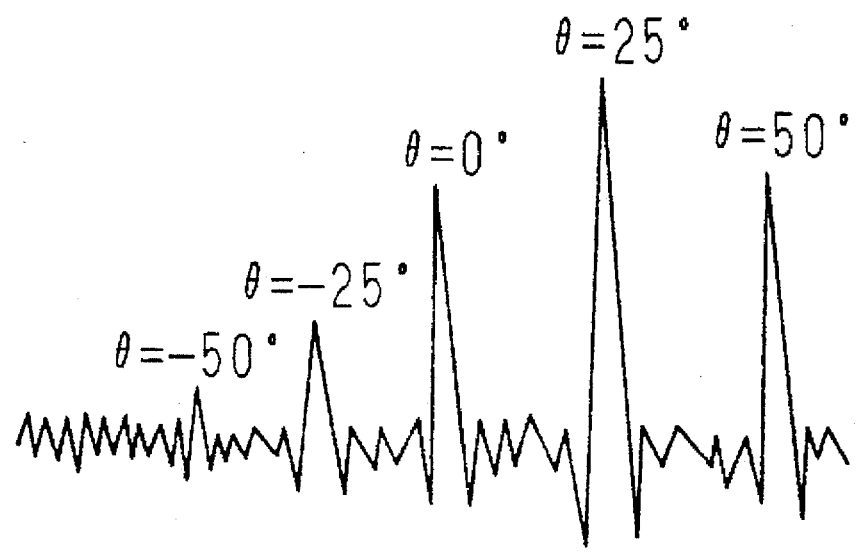
FIGS. 24(A) and 24(B) are diagrams showing waveforms representing the output signals of the two sensors in the apparatus of FIG. 13 with an object material having formed therein a plurality of flaws different only in tilt angle.
Figure 24B:
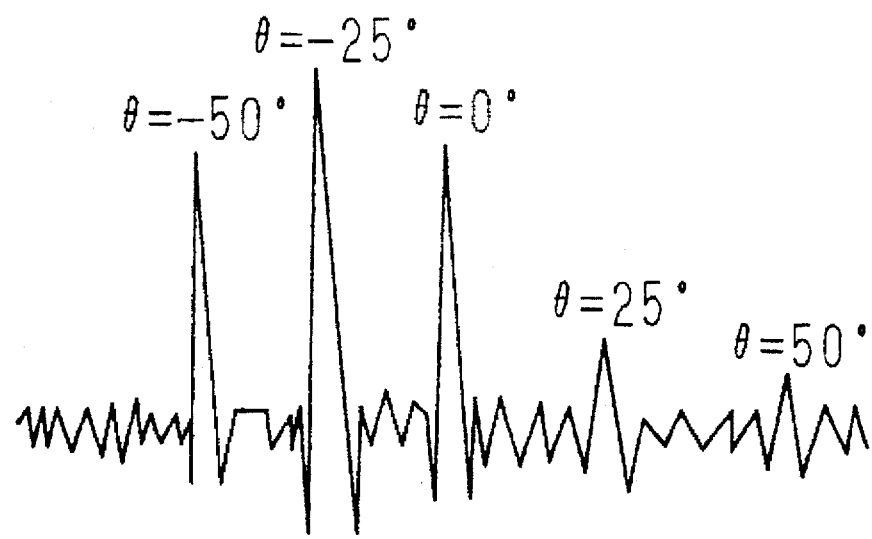

Now, explanation will be made about the result of a flaw detection test conducted with a leakage flux flaw detection apparatus according to the invention. FIGS. 24(A) and 24(B) are diagrams showing waveforms representing the sensor output signals for an object material having a plurality of flaws formed at different tilt angles by using the apparatus shown in FIG. 13. The graph of FIG. 24(A) represents an output signal of the first sensor, and FIG. 24(B) represents an output signal of the second sensor.

The object material serving as a test piece is made of a carbon steel tube on which a notched flaw 20 mm long, 0.5 mm wide and 0.5 mm deep is formed by electrical discharge machining with a tilt angle θ of −50°, −25°, 0°, +25° and +50°. A magneto diode element having a flux-sensing part with a sectional area of 1 mm×3 mm is used as the first and second sensors, and electromagnet poles are arranged with the magnetization angle φ of ±25° to search for a flaw in the test piece.

As a consequence, as shown in FIG. 24, the output of the first sensor (FIG. 24(A)) assumes a local maximum when the flaw tilt angle θ=25° and a local minimum value when the flaw tilt angle θ is −50°. The output of the second sensor (FIG. 24(B)), on the other hand, takes a local maximum value for the flaw tilt angle θ of −25° and a local minimum value for the tilt angle θ of 50°. The output ratio between the first and second sensors then is determined for each tilt angle.

Figure 25:
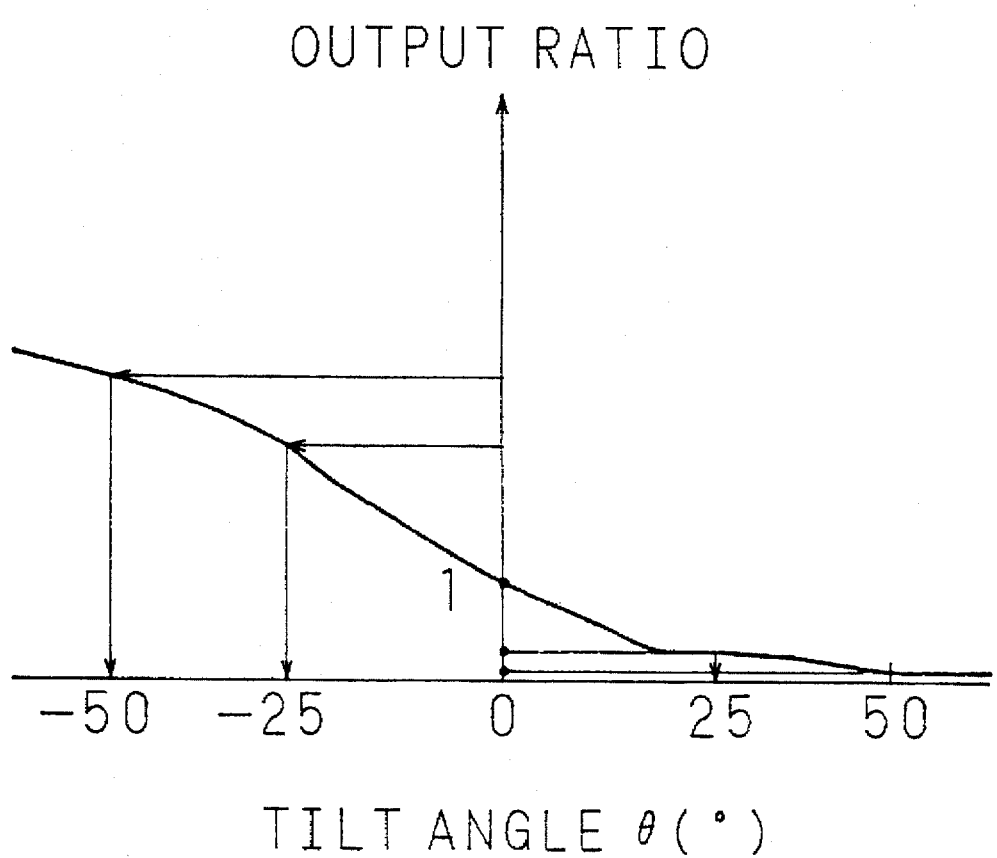
FIG. 25 is a graph showing a predetermined verification curve of the flaw tilt angle.

FIG. 25 is a graph showing a verification curve of a predetermined flaw tilt angle. The ordinate represents the output ratio, and the abscissa the tilt angle. As a result of determining a flaw tilt angle based on the output ratio between the first and second sensors and the verification curve described above, the flaw tilt angle formed by machining is found to coincide well with the tilt angle determined from the verification curve.

Figure 26:
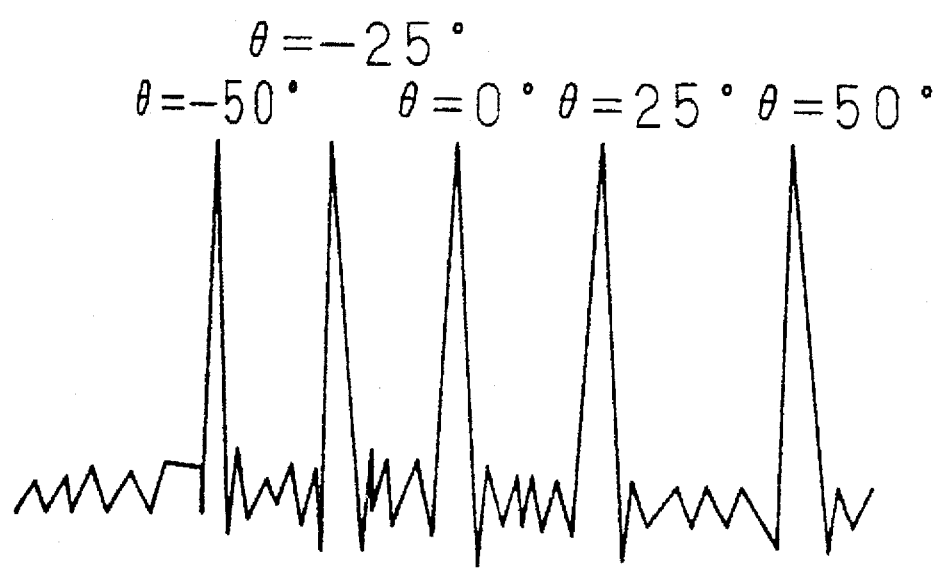
FIG. 26 is a diagram showing a waveform representing the result of correcting the outputs of the two sensors based on the flaw tilt angle.

FIG. 26 is a diagram showing waveforms representing the result of correcting the outputs of the first and second sensors on the basis of the flaw tilt angle. The reduction rate of the outputs of the two sensors with respect to the flaw tilt angle is determined in advance, and the output signal in FIG. 24 is corrected on the basis of the reduction rate thus determined. As shown in FIG. 26, the output signals of the first and second sensors have coincided with each other for all the tilt angles. Also, since the depth of each flaw formed in the object material is identical to each other as described above, the amplitudes after correction are all identical.

(First embodiment of leakage flux sensor)

Figure 27:
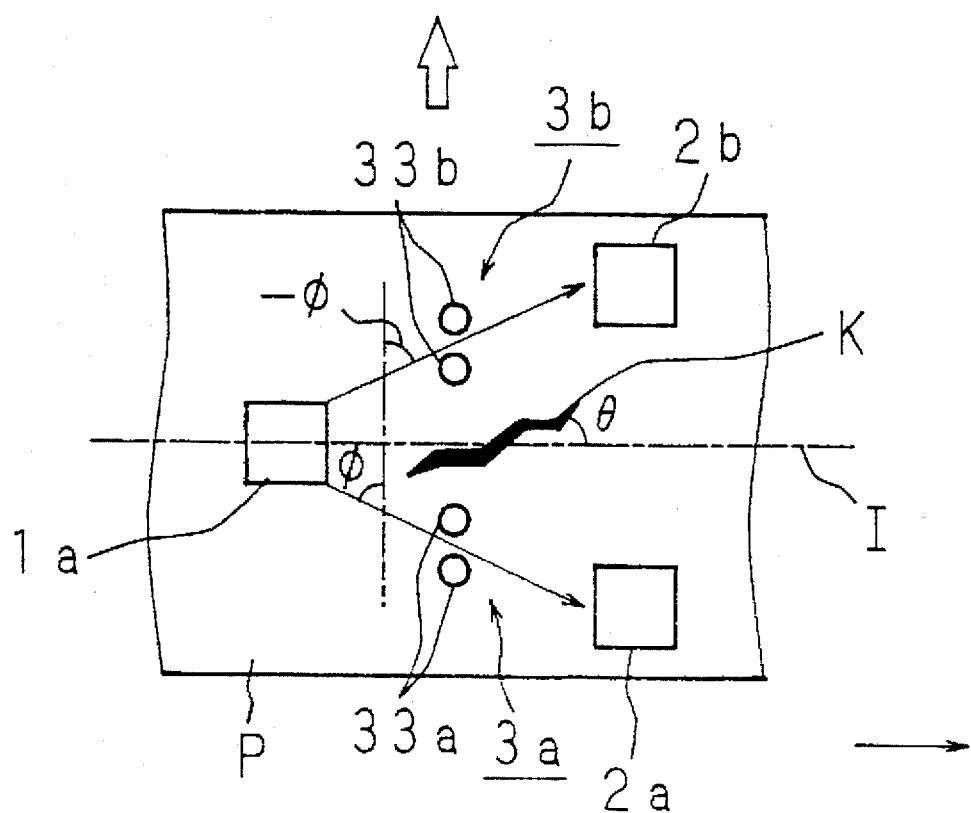
FIG. 27 is a plan view schematically showing the condition in which a flaw is being searched for using a first embodiment of a leakage flux sensor according to the invention.
Figure 28:
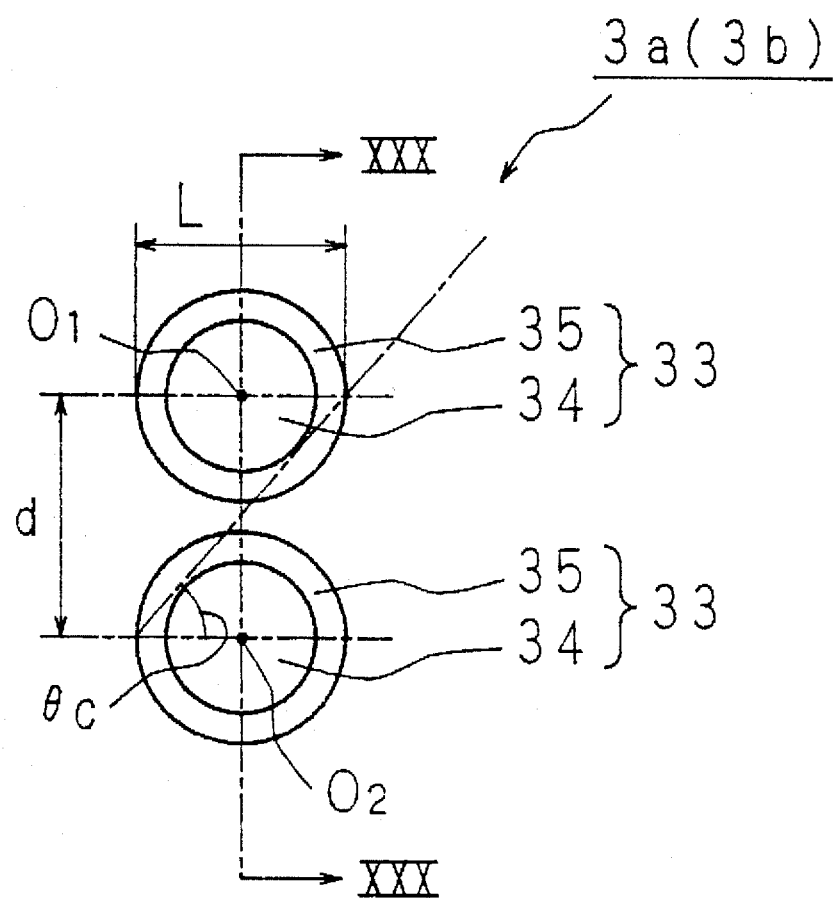
FIG. 28 is a plan view showing a first embodiment of the leakage flux sensor.
Figure 29:
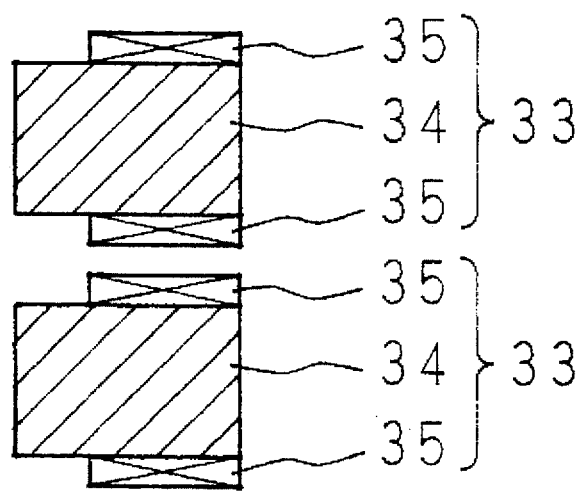
FIG. 29 is a sectional view taken in line XXX—XXX in FIG. 28.

FIG. 27 is a plan view schematically showing important parts of a leakage flux flaw detection apparatus using the first embodiment of the leakage flux sensor. In FIG. 27, the component elements identical or similar to those in FIG. 18 are designated by the same reference numerals respectively and will not be described any further. The first sensor 3a and the second sensor 3b each include two solid-cylindrical flux-sensing parts 33a, 33a and 33b, 33b respectively arranged in predetermined spaced relationship with each other in the flaw-detection direction (designated by a white arrow). The leakage fluxes due to a flaw K are detected by the flux-sensing parts 33a, 33a, 33b, 33b of the two sensors 3a, 3b respectively. The detection signals of the flux-sensing parts 33a, 33a of the first sensor 3a are applied to a flaw signal analyzer 22 (FIG. 13), where the noise signal is removed by differential operation while at the same time amplifying the flaw signal. The detection signals of the flux-sensing parts 33b, 33b of the second sensor 3b are also processed in similar fashion. FIG. 28 is a plan view showing a first embodiment of the leakage flux sensor, and FIG. 29 a sectional view taken in line XXX—XXX in FIG. 28. The sensor 3a (3b), as described above, includes two flux-sensing parts 33, 33 The flux-sensing parts 33, 33 have solid-cylindrical cores 34, 34 of ferrite arranged in predetermined spaced relationship with each other. Coils 35, 35 are wound in the vicinity of the lower end of the cores 34, 34, respectively.

The size of the flux-sensing parts 33, 33 is as follows. The distance d between centers $O_1$ and $O_2$ is not more than 4 mm, the length L of the diameter in the direction perpendicular to the flaw-detection direction is not less than 0.5 mm, and d/L not less than 1. The two flux-sensing parts 33, 33 are arranged in such a manner as to secure the distance d in the flaw-detection direction as shown in FIG. 27. The critical tilt angle $\theta_c$ of the sensor 3a (3b) is 45° to 83°. According to this embodiment, the flux-sensing parts 33, 33 are provided as a coil sensor. It is needless to say that the flux-sensing parts 33, 33 may be made alternatively of a Hall element or a magnetoresistive element with equal effect.

Figure 30:
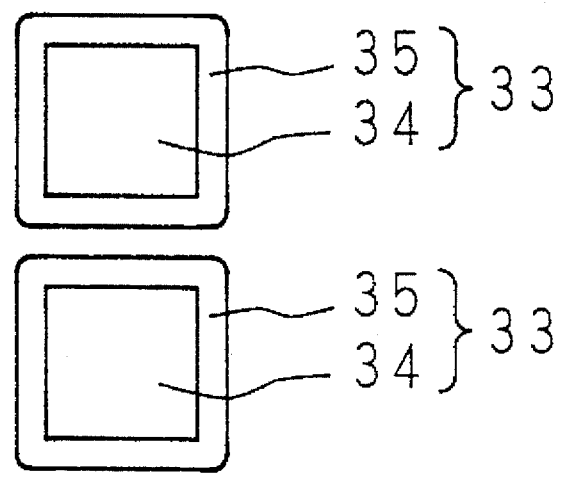
FIG. 30 is a plan view showing a modification of the first embodiment of the leakage flux sensor.
Figure 31:
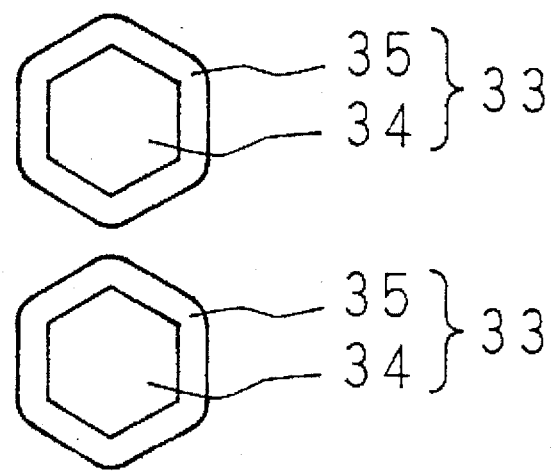
FIG. 31 is a plan view showing another modification of the first embodiment of the leakage flux sensor.

FIGS. 30 and 31 are plan views showing modifications of the first embodiment of a leakage flux sensor. The shape of the flux-sensing parts 33, 33 in plan view may be a square as shown FIG. 30 or a polygon such as a regular hexagon shown in FIG. 31 as well as a circle shown in FIG. 28. In this way, the detection signals of the two flux-sensing parts 33, 33 are kept at substantially the same level regardless of the flaw tilt angle θ by making the plan view of the flux-sensing parts 33, 33 a circle or a regular polygon.

Figure 32:
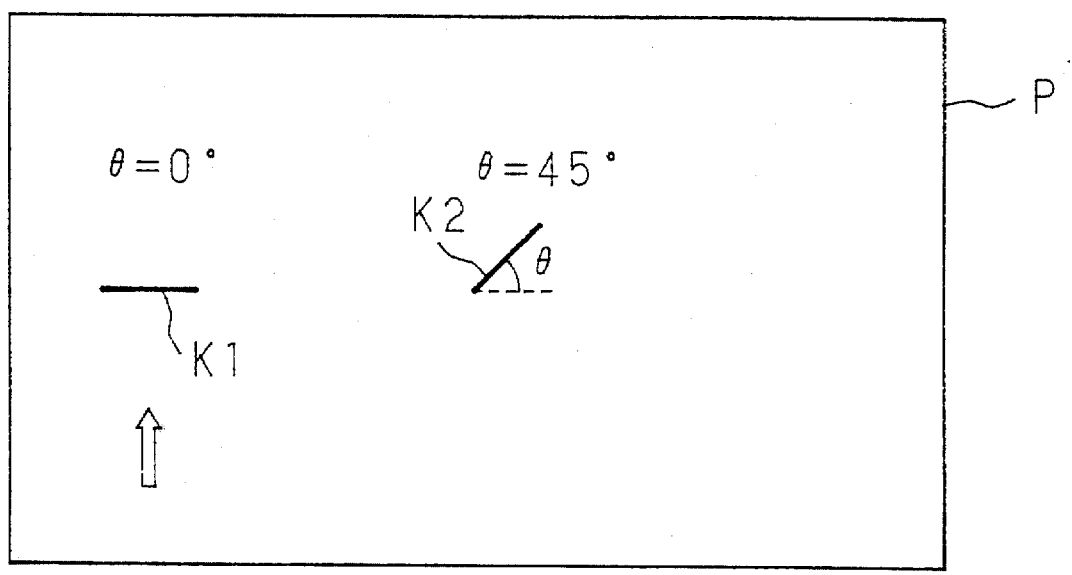
FIG. 32 is a plan view showing an object material.

Now, explanation is made about a test example using a first embodiment of the leakage flux sensor. This test was conducted on a tabular material. FIG. 32 is a plan view showing an object material. The object material P is made of a rectangular carbon steel sheet 5 mm thick on the surface of which notched flaws K1, K2 with the thickness of 5 mm, length of 20 mm, width of 0.5 mm and depth of 0.5 mm are formed with a tilt angle of 0° or 45° by electrical discharge machining. As shown by the white arrow in the drawing, flaws are searched for in the direction perpendicular to the notched flaw K1 with the tilt angle θ of 0°.

Figure 33:
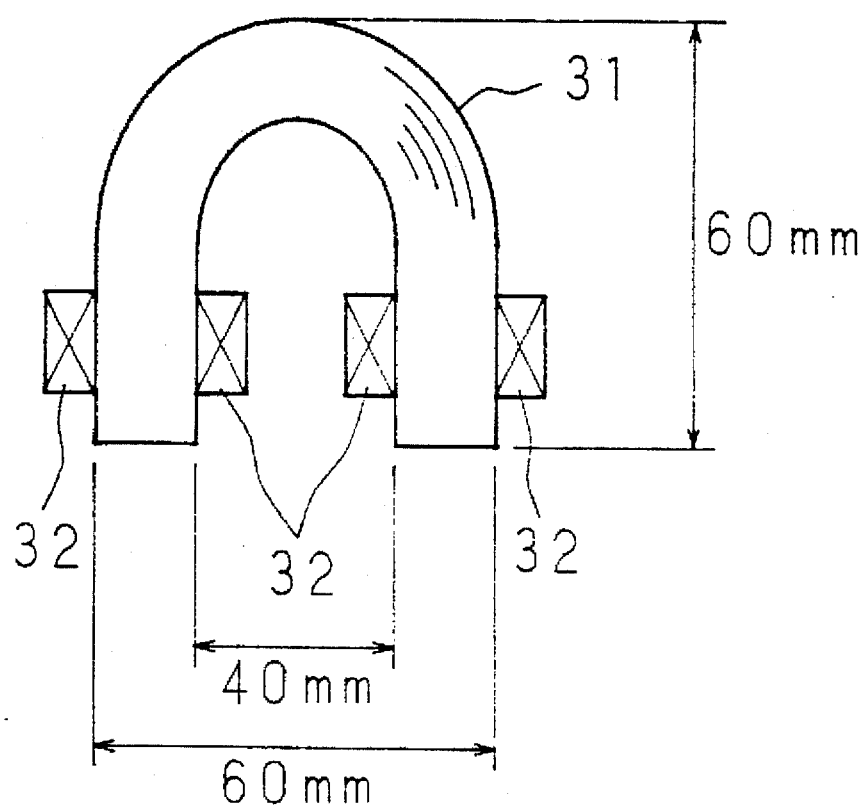
FIG. 33 is a side view showing an electromagnet pole for magnetizing an object material.

FIG. 33 is a side view showing an electromagnet pole unit for magnetizing an object material. In FIG. 33, numeral 31 designates a U-shaped core. The U-shaped core 31 is formed of a plurality of silicon steel sheets laminated in U shape (outer length of open legs 60 mm×inner length of open legs 40 mm×height 60 mm×length 65 mm), with the two legs wound with coils 32, 32 of copper conductors (outer diameter of 1 mm) in 30 turns, respectively. The magnetizing power is 3 (A)×60 (T)=180 (A·T), and the excitation frequency 2 kHz. In order to keep a constant value of the magnitude of the leakage fluxes from each of the notched flaws K1, K2 shown in FIG. 32, the notched flaws K1, K2 are magnetized in the direction perpendicular to the length thereof.

Figure 10:
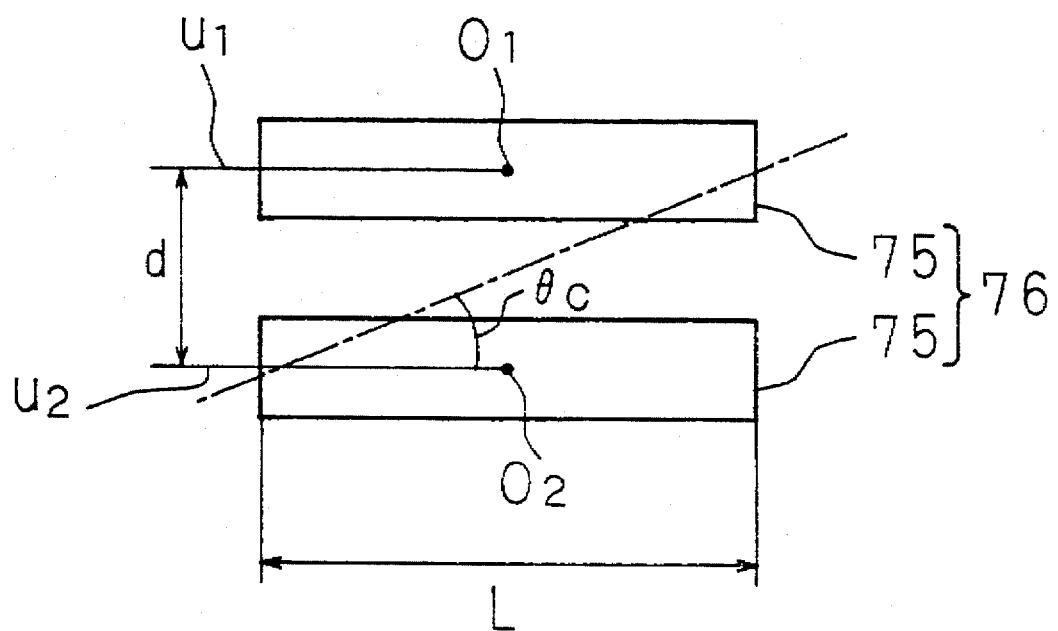
FIG. 10 is a plan view schematically showing a conventional leakage flux sensor.
Figure 11:
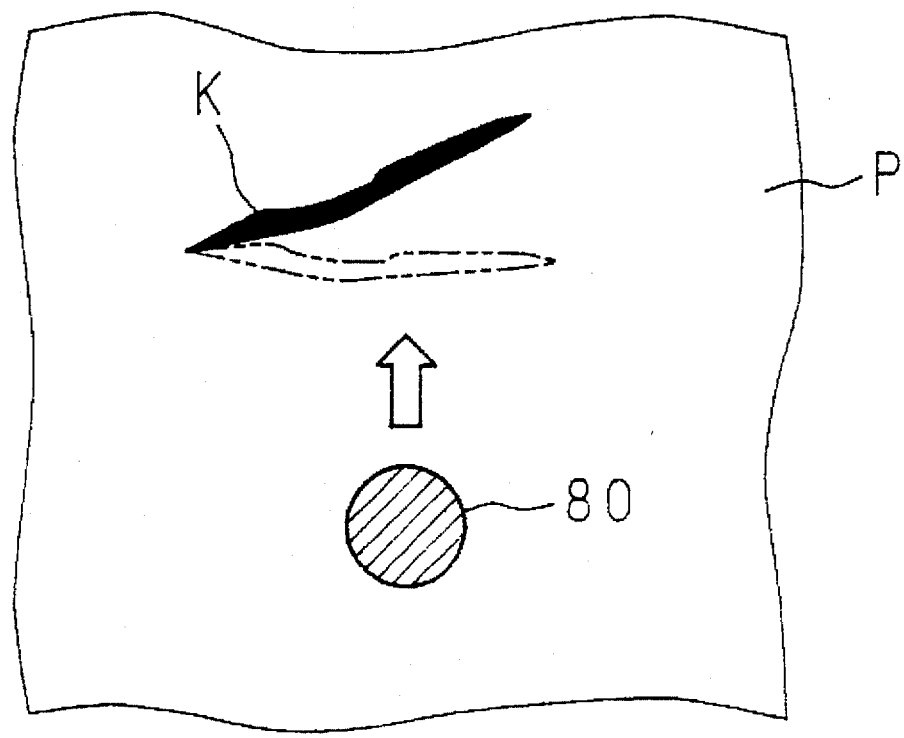
FIG. 11 is a diagram for explaining a conventional method for preventing the signal amplitude reduction caused by the flaw tilt angle.
Figure 12A:
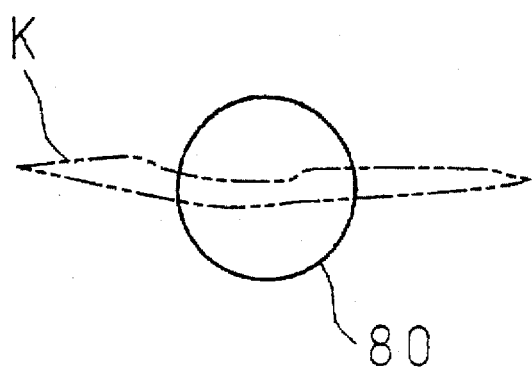
FIGS. 12(A) and 12(B) are diagrams for explaining that the reduction of the signal amplitude can be prevented by a conventional method using flux-sensing parts having a circular cross section.
Figure 12B:
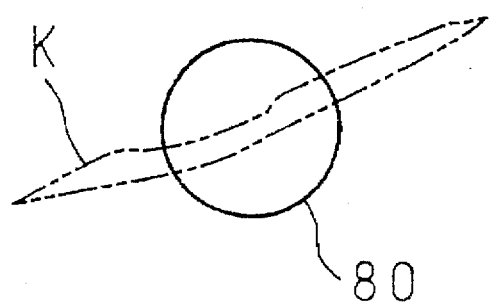

The sensor for detecting leakage fluxes according to this embodiment includes circular flux-sensing parts as shown in FIG. 28, of which the center distance d is 3 mm, the size L in the direction perpendicular to the flaw-detection direction is 2 mm and the critical tilt angle $\theta_c$ about 56°. An example of conventional apparatuses, on the other hand, includes rectangular flux-sensing parts as shown in FIG. 10 with the center distance d of 3 mm, the size L of 1 mm and the critical tilt angle $\theta_c$ of about 18°.

Figure 34A:
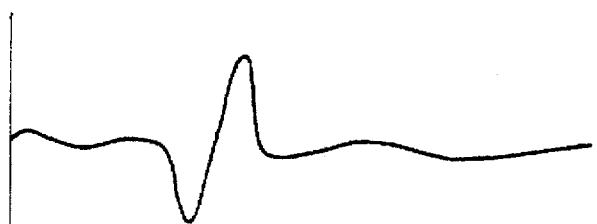
FIGS. 34A–34D are diagrams showing waveforms of detection signals from a conventional leakage flux sensor and signals obtained by differential operation between the two detection signals.
Figure 34B:
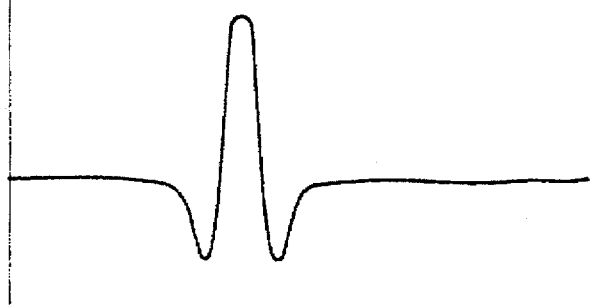

FIGS. 34A–34D are graphs showing detection signals by the conventional sensor, and FIGS. 25A–35D are graphs showing detection signals by a sensor according to this embodiment. FIG. 34(a) and FIG. 35(a) represent a detection signal of a notched flaw with a tilt angle θ of 0° detected by one of the flux-sensing parts, FIG. 34(b) and FIG. 35(b) signals obtained by differential operation between two detection signals of a notched flaw with a tilt angle θ of 0° produced by two flux-sensing parts, FIGS. 34(c) and 35(c) detection signals of a notched flaw with a tilt angle θ of 45° produced by one of the flux-sensing parts, and FIGS. 34(d) and 35(d) signals obtained by differential operation between two detection signals of a notched flaw with a tilt angle θ of 45° produced by two flux-sensing parts.

Figure 34C:
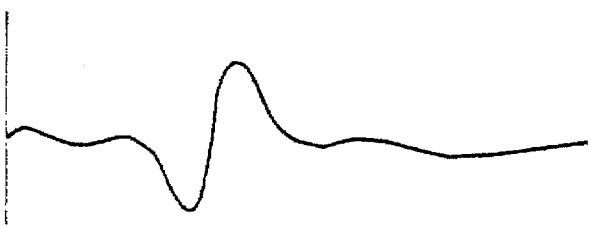
Figure 34D:
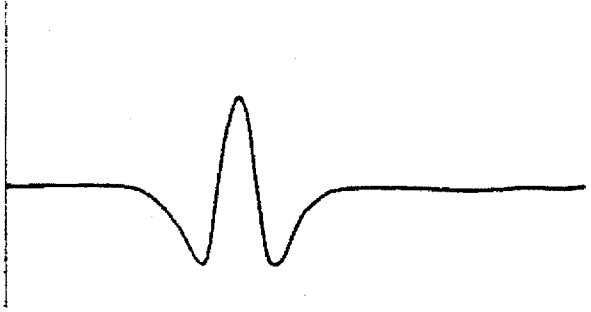

As seen from FIGS. 34(a) and 34(c), in the conventional sensor, the flaw signal with a tilt angle θ of 45° is smaller in amplitude than the flaw signal with a tilt angle θ of 0° so that the detection sensitivity varies with the flaw tilt angle θ. Also, as obvious from FIGS. 34(b) and 34(d), after differential operation between detection signals produced from the two flux-sensing parts, the flaw signal with a tilt angle θ of 45° exceeds the critical tilt angle $\theta_c$ and therefore, as compared with the flaw signal with a tilt angle θ of 0°, is small in amplitude by about 70%.

With the sensor according to the present embodiment, as seen from FIGS. 35(a) and 35(c), the amplitude of a flaw signal with a tilt angle θ of 45° is substantially the same as that of a flaw signal with a tilt angle θ of 0°. Also, it is seen from FIGS. 35(b) and 35(d) that differential operation between detection signals produced from the two flux-sensing parts leads to a critical tilt angle $\theta_c$ of about 56° and therefore amplifies the flaw signal with θ of 45° to the same degree as the flaw signal with a tilt angle θ of 0°.

Figure 36:
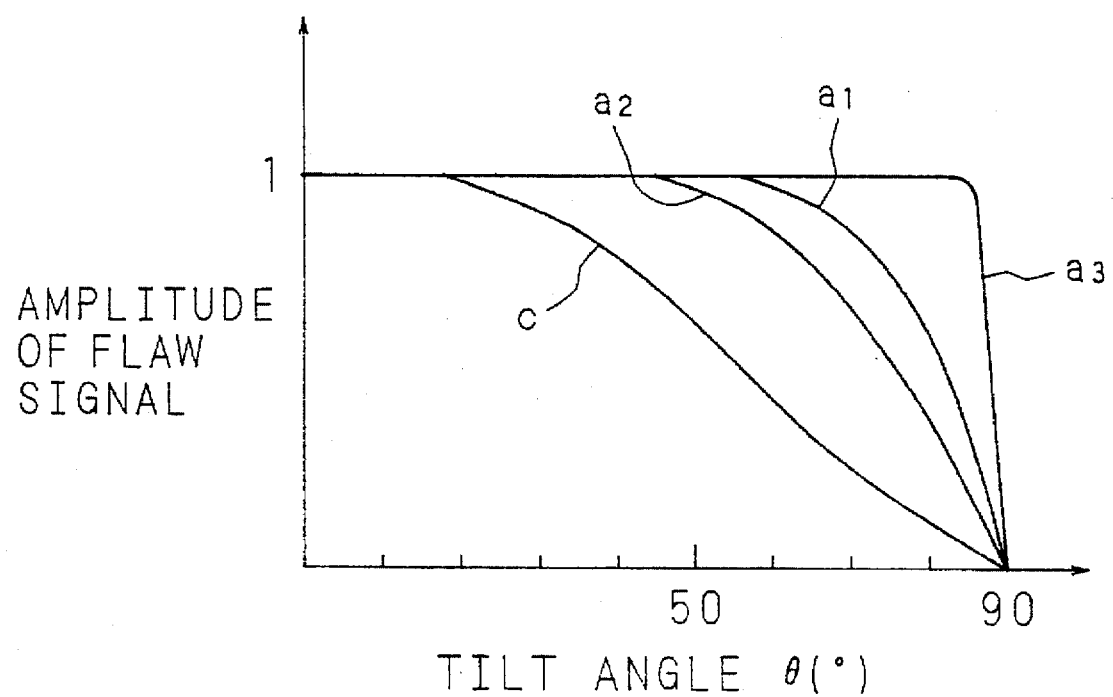
FIG. 36 is a graph showing the relation between the flaw tilt angle and the amplitude of a flaw signal, FIGS. 37(A) and (B) are a longitudinal sectional view of a leakage flux sensor according to a second embodiment of the invention and a sectional view taken in line XXXVII—XXXVII in FIG. 37(A), respectively, FIGS. 38(A) and (B) are diagrams for explaining relative positions of a second embodiment of a leakage flux sensor and a flaw.

FIG. 36 is a graph showing the detection result of a notched flaw formed by changing the tilt angle θ at intervals of 10° in the tilt angle range of 0° to 90°. In FIG. 36, character c designates the result obtained by the above-mentioned conventional sensor, and a1 the result obtained by the above-mentioned sensor according to this embodiment. Also in FIG. 36, a2 and a3 designate the result obtained by sensors according to this embodiment, of which a2 is the result obtained by a sensor having a center distance d of 3 mm between two flux-sensing parts, a size L of 2 mm in the direction perpendicular to the flaw-detection direction and a critical tilt angle $\theta_c$ of about 45°, while a3 is the result obtained by a sensor having a center distance d of 3 mm, a size L of 2 mm and a critical tilt angle θc of about 83°. The abscissa represents the tilt angle θ, and the ordinate the amplitude of a flaw signal shown with the amplitude of a flaw signal having a tilt angle θ of 0 as 1.

It is seen from FIG. 36 that in the conventional sensor the flaw signal sharply decreases from the tilt angle θ of 20° so that the range of tilt angles that can be accommodated by the conventional sensor is very narrow. In all the sensors according to the present embodiment, on the other hand, the flaw signal remains substantially the same in magnitude up to the respective critical tilt angle $\theta_c$ thereof, with the result that the flaw detection requirement can be met down to a tilt angle $\theta$ of 45° in minimum and up to a tilt angle $\theta$ of 83° in maximum.

(Second embodiment of leakage flux sensor)

Figure 37A:
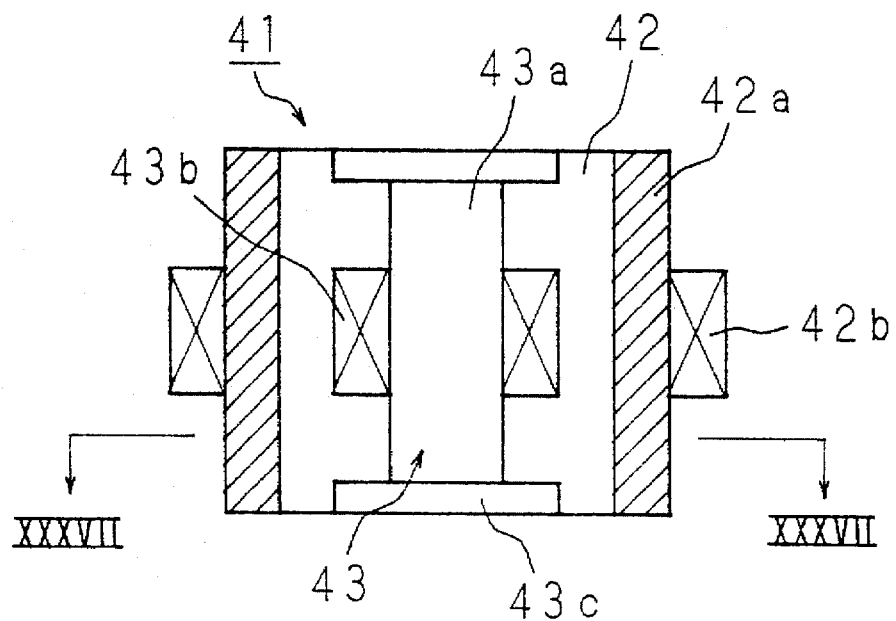
Figure 37B:
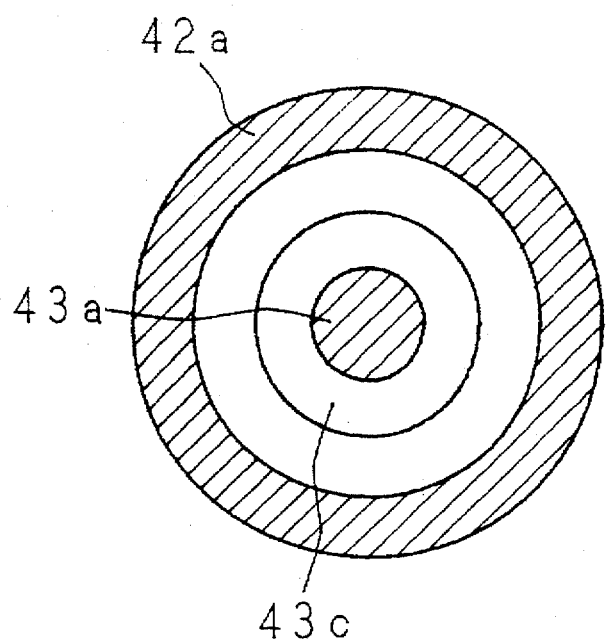

A leakage flux sensor according to a second embodiment of the invention is described below. FIG. 37 is a diagram showing an example of the leakage flux sensor according to the second embodiment. FIG. 37(A) is a longitudinal sectional view, and FIG. 37(B) a sectional view taken in line XXXVII—XXXVII in FIG. 37(A).

As shown in FIGS. 37(A) and 37(B) leakage flux sensor 41 includes a hollow-cylindrical first flux-sensing part 42 and a solid-cylindrical second flux-sensing part 43 provided in the hollow portion of the first flux-sensing part 42 along the same axis. The first flux-sensing part 42 is formed of a conductor 42b (outer diameter of 0.5 mm) of copper or the like wound (in 20 turns) on the outer periphery of the central portion along the axis of a hollow-cylindrical ferrite core 42a (outer diameter of 6 mm, inner diameter of 5 mm and a height of 5 mm). The second flux-sensing part 43, on the other hand, is formed of a conductor 43b (outer diameter of 0.5 mm) of copper or the like wound (in 20 turns) on the outer periphery of the axial part of a solid-cylindrical ferrite core 43a (axial outer diameter of 2 mm and a height of 5 mm including the flange) with a flange 43c (outer diameter of 4 mm and a thickness of 0.5 mm) formed at each end thereof.

Figure 38A:
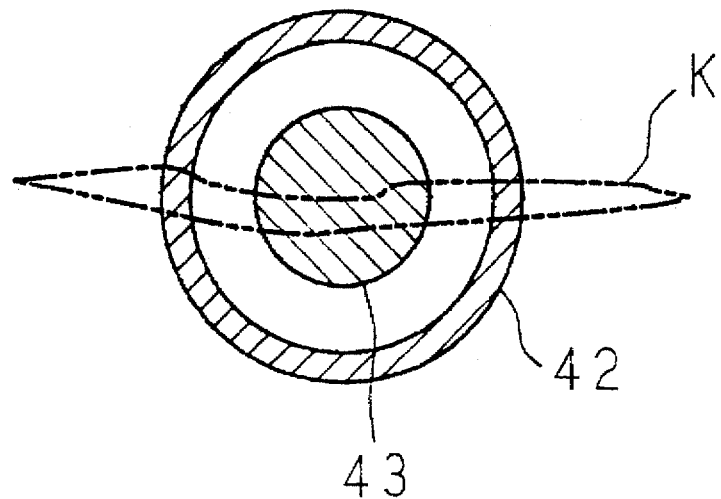
Figure 38B:
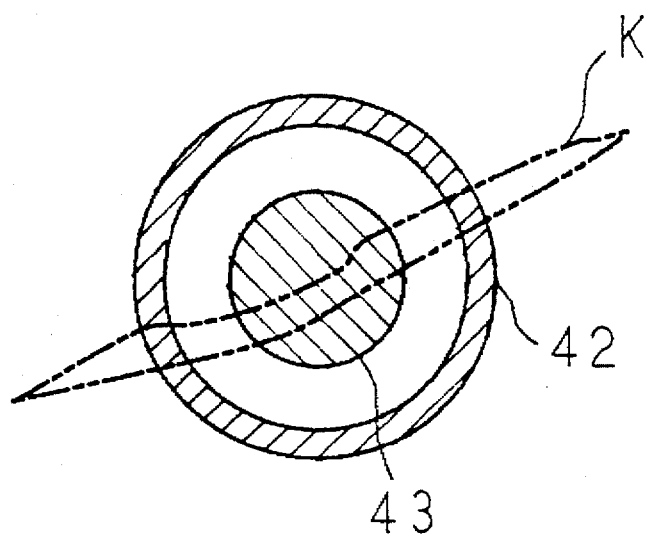

Assume that a linear flaw K extending in a predicted direction is to be searched for by scanning in a direction perpendicular to the predicted direction using the leakage flux sensor 41 configured of the first flux-sensing part 42 and the second flux-sensing part 43 having a circular cross section disposed concentrically. Even in the case where an actual flaw K is tilted in a direction different from the predicted direction, the detection sensitivity is not reduced. This is by reason of the fact that as shown in FIGS. 38(A) and (B), with a flaw K having the same shape and the same depth, the relative positions of the first flux-sensing part 42 and the second flux-sensing part 43 with respect to the flaw K become constant at the same time in a horizontal Diane around the axis thereof, and therefore that the flux-sensing parts 42, 43 produce a flaw signal of a predetermined amplitude at the same time corresponding to the amount of leakage fluxes sensed in accordance with the size of the cross sectional area of the ferrite cores 42a, 43a, respectively, regardless of the direction in which the flaw K extends.

The output amplitude of noise signals including a loose material signal (e.g., a signal caused by loose material on the surface of the object material, surface unevenness; or transportation vibrations of an object material) can be suppressed using the differential connection of the two flux-sensing parts 42, 43 as in the prior art and the above-mentioned embodiment.

Figure 39:
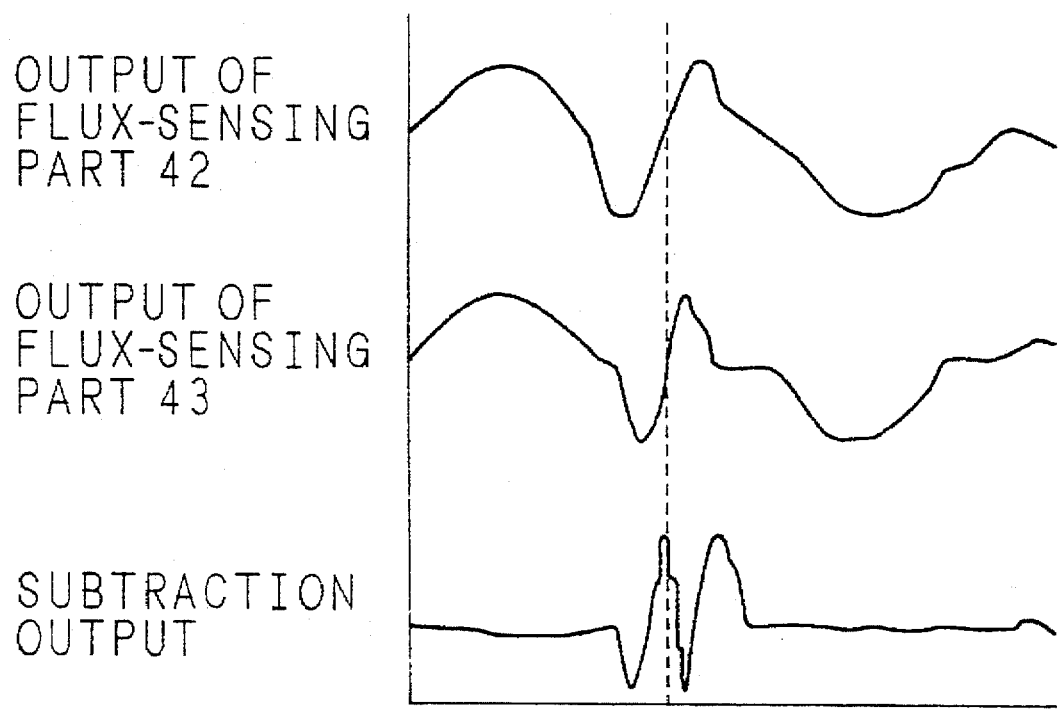
FIG. 39 is a diagram showing waveforms representing detection signals according to a second embodiment of the leakage flux sensor and a signal obtained by differential operation between the two detection signals.

FIG. 39 is a diagram showing an example of a flaw signal waveform of the first flux-sensing part 42 and the second flux-sensing part 43 configured as described above, and also an example of a flaw signal waveform of the two flux-sensing parts 42, 43 concentrically arranged and differentially connected. As seen from FIG. 39, the flaw signal waveforms for the first flux-sensing part 42 and the second flux-sensing part 43, both of which have a circular cross section, are seen to have a predetermined amplitude for a linear flaw of a predetermine shape and a predetermined depth, regardless of the direction in which the particular linear flaw extends. Also, it is seen that with the flaw signal waveforms obtained when the two flux-sensing parts 42, 43 are concentrically arranged and differentially connected, the noise signal thereof due to the loose material signal, a gentle change of magnetic field or the like is suppressed.

Figure 40:
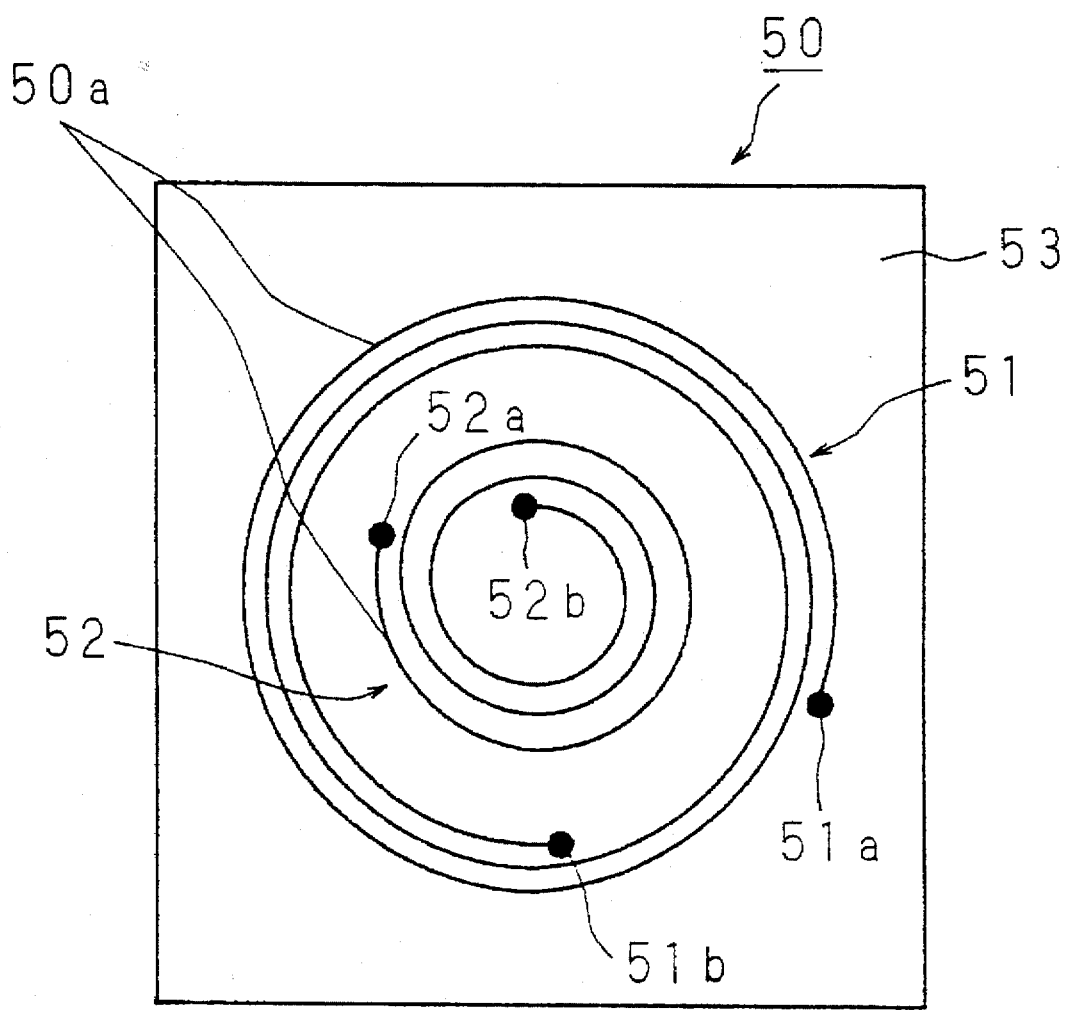
FIG. 40 is a plan view showing a modification of a leakage flux sensor according to a second embodiment.

FIG. 40 is a plan view showing a modification of the leakage flux sensor according to the second embodiment. As seen from FIG. 40, the leakage flux sensor 50 in this example includes a first coil 51 large in diameter and a second coil 52 small in diameter concentrically arranged and printed on a silicon wafer 53 with a conductor 50a of copper or the like wound spirally in a plurality of turns at predetermined spatial intervals. Numerals 51a, 52a in FIG. 40 designate an input terminal, and 51b, 52b an output terminal. It is needless to say that a substantially similar flaw signal waveform to that of FIG. 39 can be obtained with the leakage flux sensor 50 according to this modification which includes the large-diameter first coil 51 and the small-diameter second coil 52 arranged and printed concentrically on the silicon wafer 53.

Figure 41A:
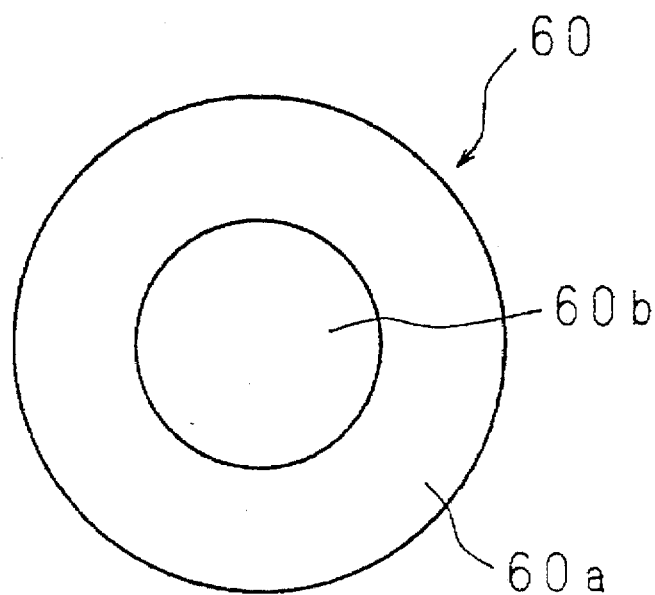
FIGS. 41(A) and 41(B) are a plan view and a side sectional view respectively showing another modification of a second embodiment of the leakage flux sensor.
Figure 41B:
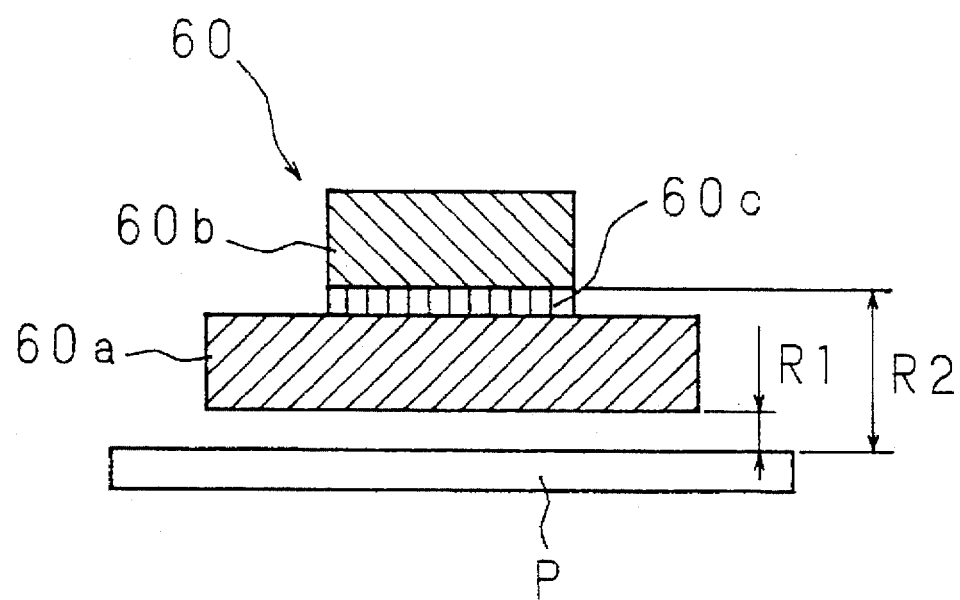

FIG. 41 is a diagram showing another modification of the leakage flux sensor according to the second embodiment. FIG. 41(A) is a plan view, and FIG. 41(B) a side sectional view. As shown in FIG. 41, a leakage flux sensor 60 according to this modification is an example with a magnetic sensor including a flux-sensing element such as a Hall probe or a magnetoresistive element. This sensor includes a first flux-sensing part 60a and a second flux-sensing part 60b having a circular cross section with different sectional areas laminated in vertical direction along the same axis through an insulating layer 60c disposed therebetween.

In the leakage flux sensor 60 shown in FIG. 41, the first flux-sensing part 60a and the second flux-sensing part 60b can be formed in reverse layers. Also, as seen from this example, the coil-type leakage flux sensor 41 shown in FIG. 37 may be configured of a vertical lamination including a solid-cylindrical flux-sensing part having a large sectional area as the first flux-sensing part 42 and a second flux-sensing part 43 of a solid material having a small sectional area. This laminated sensor has different lift-offs R1, R2 for the flux-sensing parts 60a, 60b with respect to the surface of the object material P (FIG. 41(B)), resulting in different detection sensitivities. In view of this, calibration of course is required to ensure that signals from the same flaw can be detected with the same sensitivity.

Figure 1:
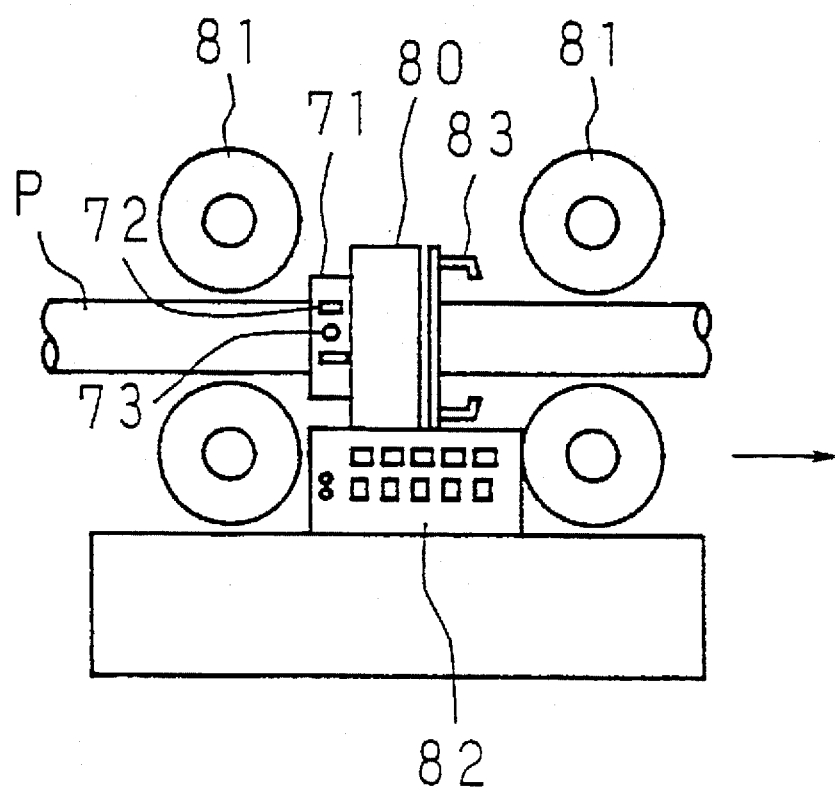
FIG. 1 is a side view schematically showing a conventional leakage flux flaw detection apparatus of rotary type.
Figure 2:
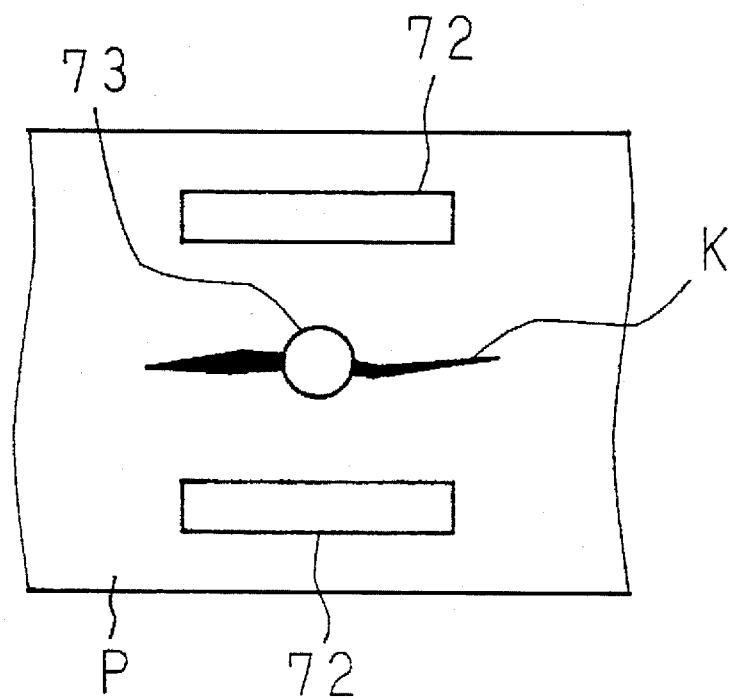
FIG. 2 is a partially enlarged view of the model shown in FIG. 1.
Figure 3:
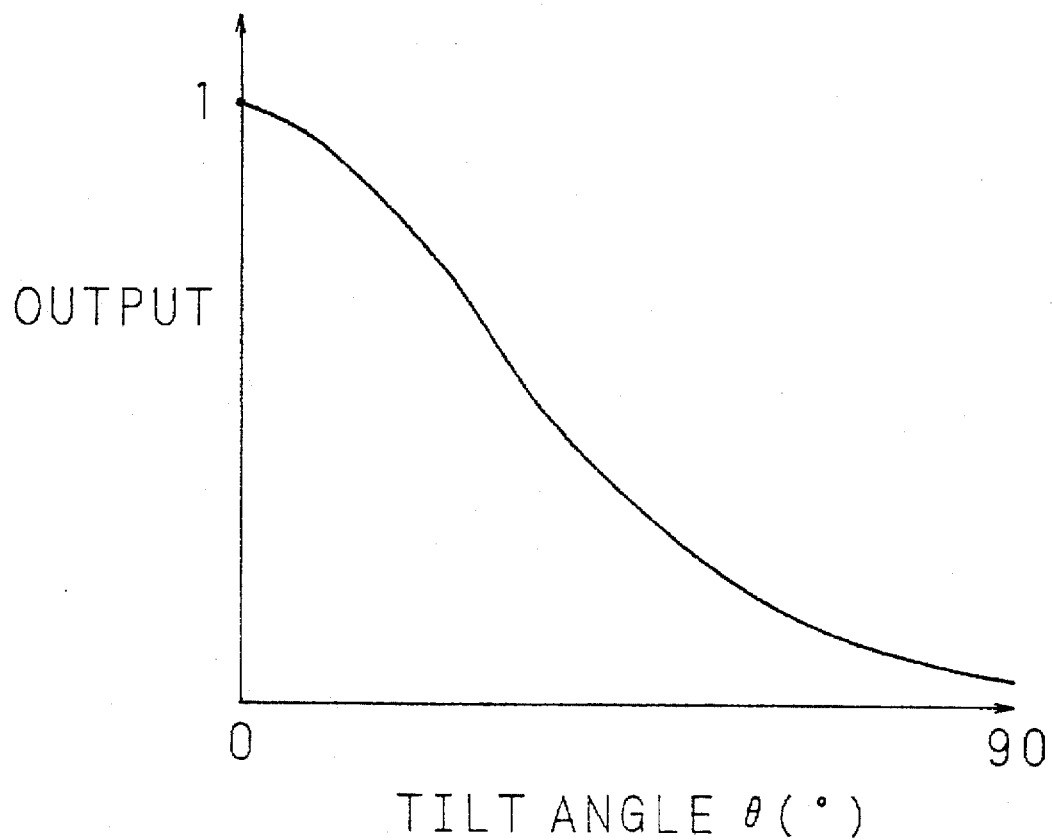
FIG. 3 is a graph showing the relation between the flaw tilt angle and the sensor output.
Figure 4:
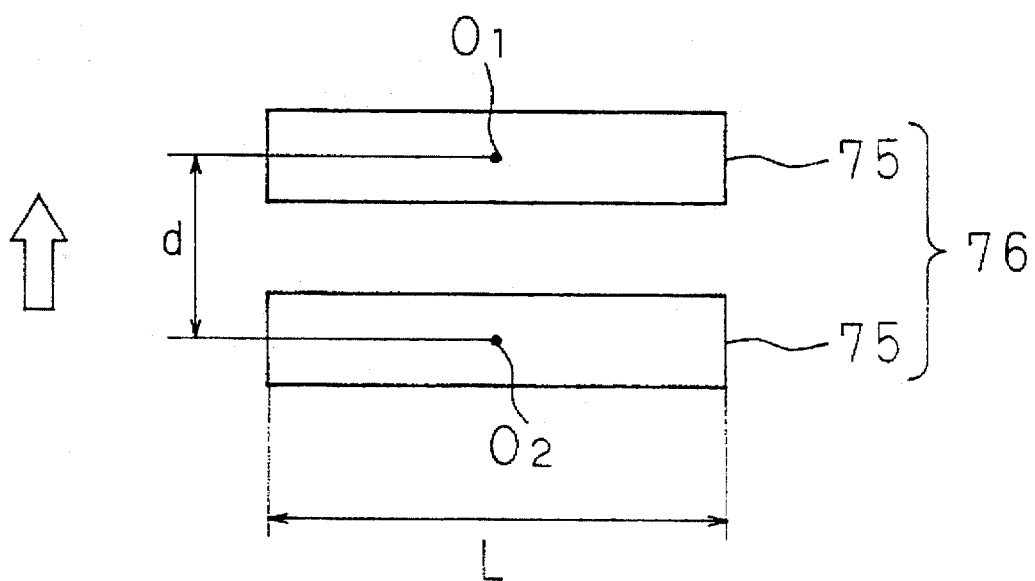
FIG. 4 is a plan view schematically showing a conventional leakage flux sensor.
Figure 5:
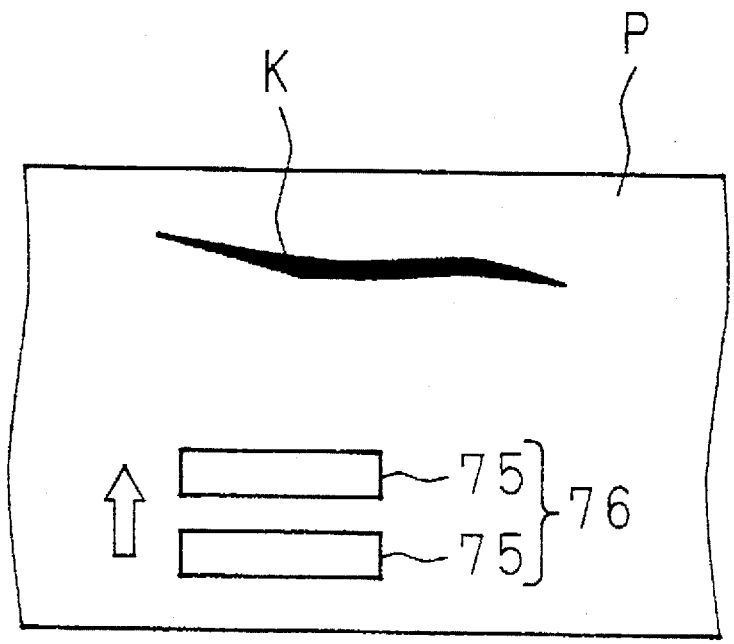
FIG. 5 is a plan view showing the condition in which a flaw is being searched for by the sensor shown in FIG. 4.
Figure 6:
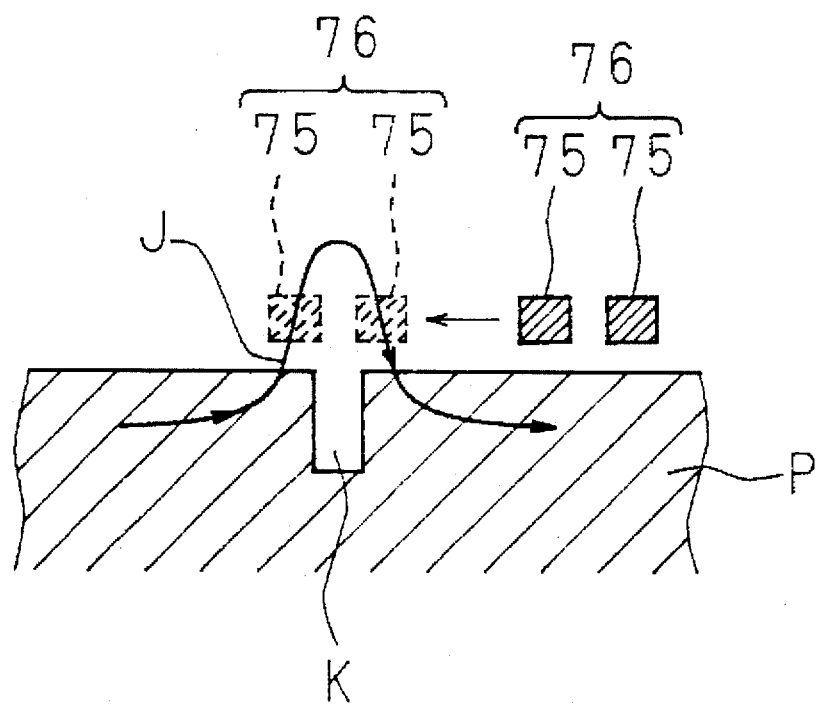
FIG. 6 is a side view showing the condition in which a flaw is being searched for by the sensor shown in FIG. 4, FIGS. 7A–7C showing waveforms of the detection signals of the flux-sensing parts of the sensors shown in FIG. 6 and the signals subjected to differential operation between the two detection signals.
Figure 7A:
Figure 7B:
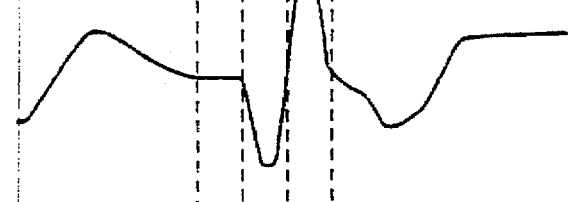
Figure 7C:
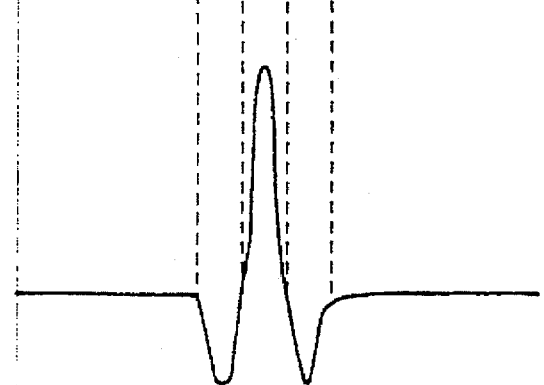
Figure 8:
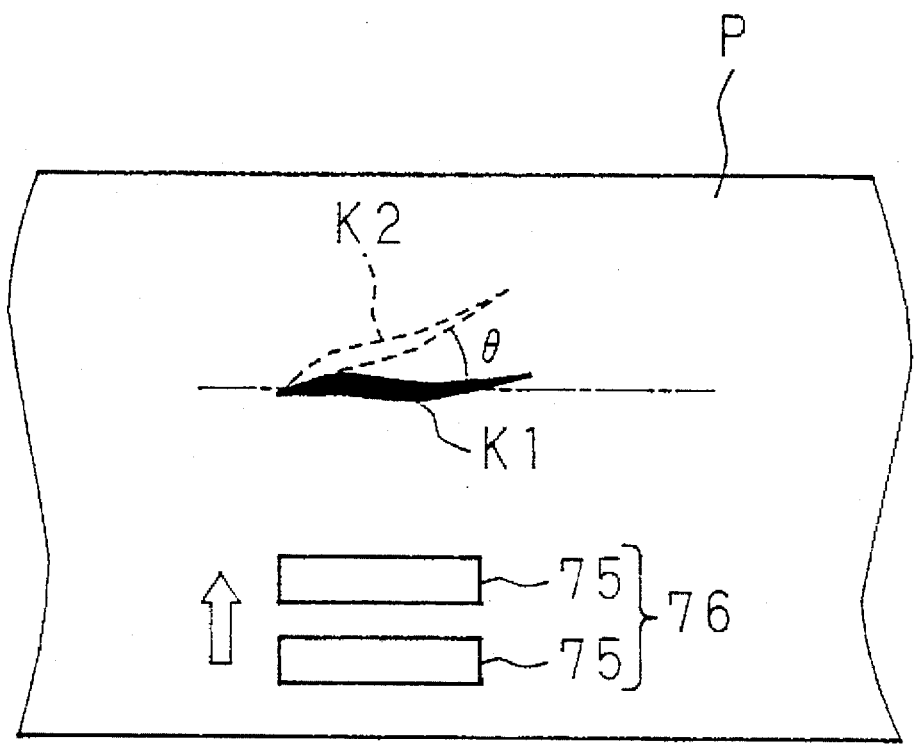
FIG. 8 is a plan view showing the relation between a sensor having two flux-sensing parts and the tilt of a flaw.
Figure 9:
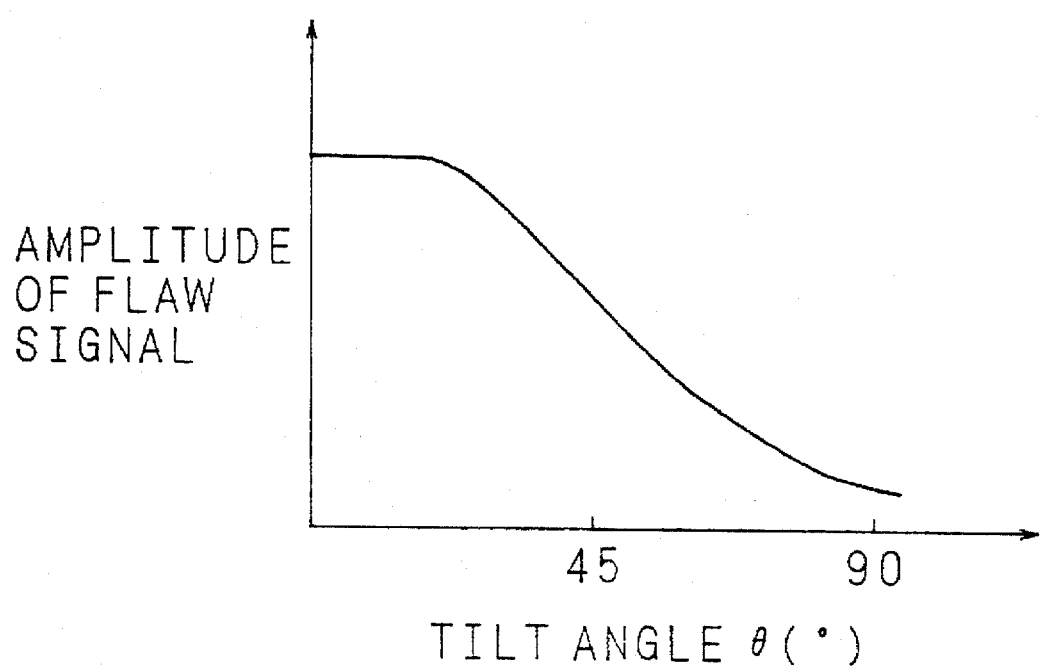
FIG. 9 is a graph showing the relation between the flaw tilt angle and the amplitude of a flaw signal in a conventional leakage flux sensor.
Figure 42:
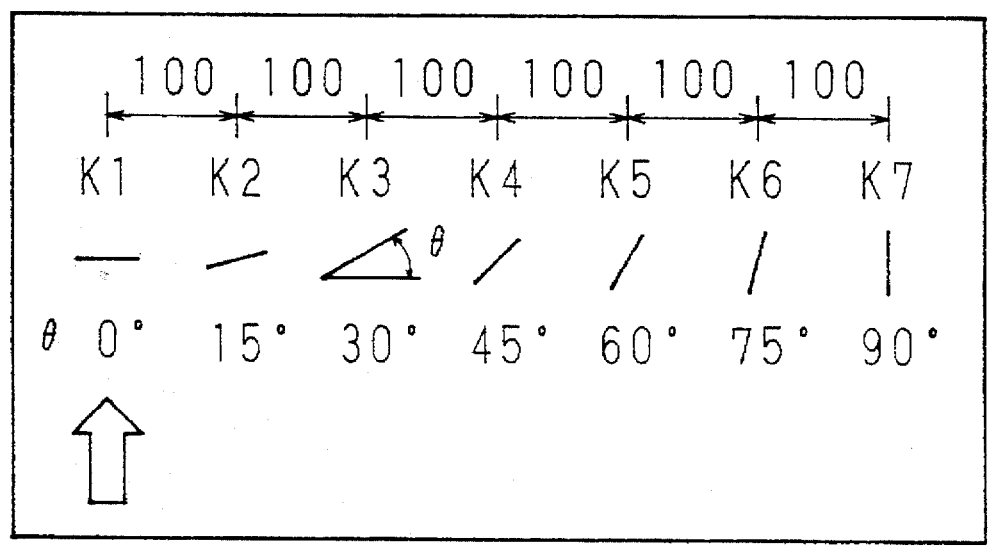
FIG. 42 is a plan view showing an object material.

Now, explanation is made about the result of a test conducted on a leakage flux sensor according to the second embodiment. An object material is prepared which, as shown in FIG. 42, is made of a 5 mm-thick carbon steel sheet processed by electrical discharge machining, whereby notched artificial flaws (20 mm long×0.5 mm wide and 0.5 mm deep) K1 to K7 are formed with counterclockwise tilt angles $\theta$ of 0° to 90° with a 15° pitch from the direction of extension of the leftmost flaw (K1) as a reference. Then, the object material is magnetized under the conditions of 2 kHz in exciting frequency and 3 (A)×60 (T)=180 (A·T) in magnetizing force using a magnetizing electromagnet pole of AC type shown in FIG. 33 as described above. After that, the flaws K1 to K7 are searched for in the scanning direction along the white arrow in FIG. 42 using the leakage flux sensor 41 according to the present embodiment which is in the shape shown in FIG. 37 and has the above-mentioned dimensions. Also, by way of comparison, each flaw is searched for by a similar method using a conventional leakage flux sensor configured as shown in FIG. 5 and having a rectangular cross section with a long side of 4 mm and a short side of 1 mm.

Figure 43A:
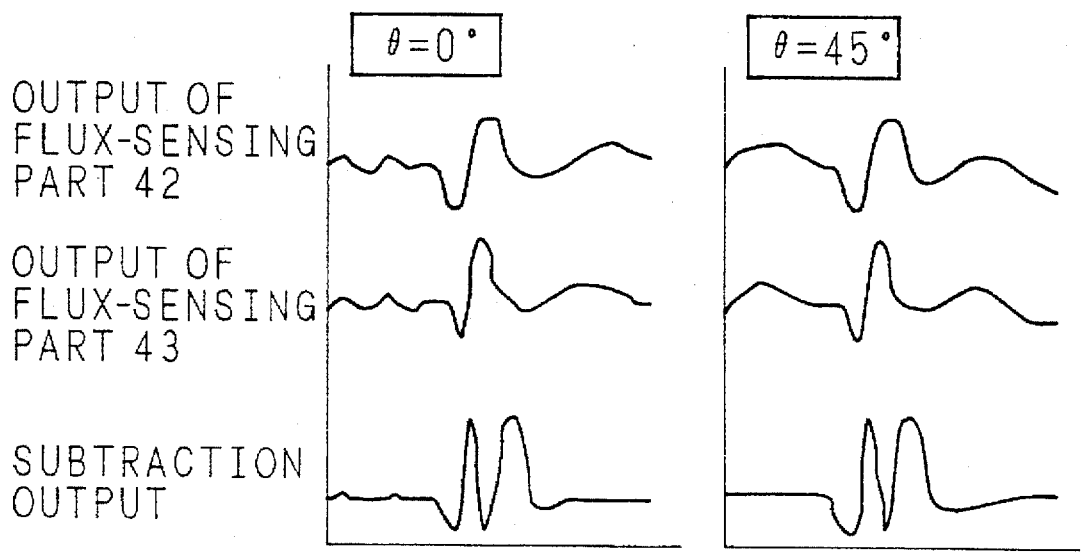
FIG. 43(A) is a diagram showing waveforms of detection signals according to a second embodiment of the leakage flux sensor and a detection signal obtained by differential operation between the two detection signals.
Figure 43B:
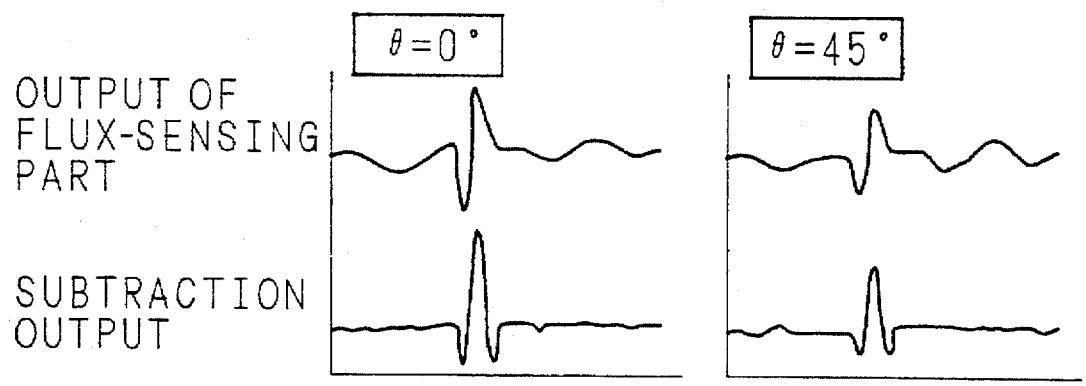
FIG. 43(B) is a diagram showing waveforms of a detection signal and a detection signal obtained by differential operation between two detection signals in a conventional leakage flux sensor.

FIG. 43 shows detection signal waveforms produced from each flux-sensing part and detection signal waveforms subjected to the differential operation between them for the artificial flaw K1 having a tilt angle θ of 0° and the artificial flaw K4 having a tilt angle θ of 45°. FIG. 43(A) represents the case using a leakage flux sensor according to this embodiment, and FIG. 43(B) the case using the conventional leakage flux sensor. In the latter case handling the prior art, the outputs of the two flux-sensing parts are identical, and therefore the outputs of one of the flux-sensing parts is shown in FIG. 43(B).

As seen from FIGS. 43(A) and 43(B) in the conventional leakage flux sensor, the amplitude of a flaw signal of the artificial flaw K4 having a tilt angle θ of 45° is reduced to about 70% of the amplitude of the flaw signal having a tilt angle θ of 0°. With the leakage flux sensor according to the present embodiment, in contrast, the amplitude of the flaw signal is not reduced. Also, with either the conventional leakage flux sensor and the leakage flux sensor according to this embodiment, the above-mentioned noise signal is not substantially observed in the signal waveform after the differential operation although it is observed that the signal waveform of each flux-sensing part contains a noise signal caused by a gentle change of magnetic field.

Figure 44:
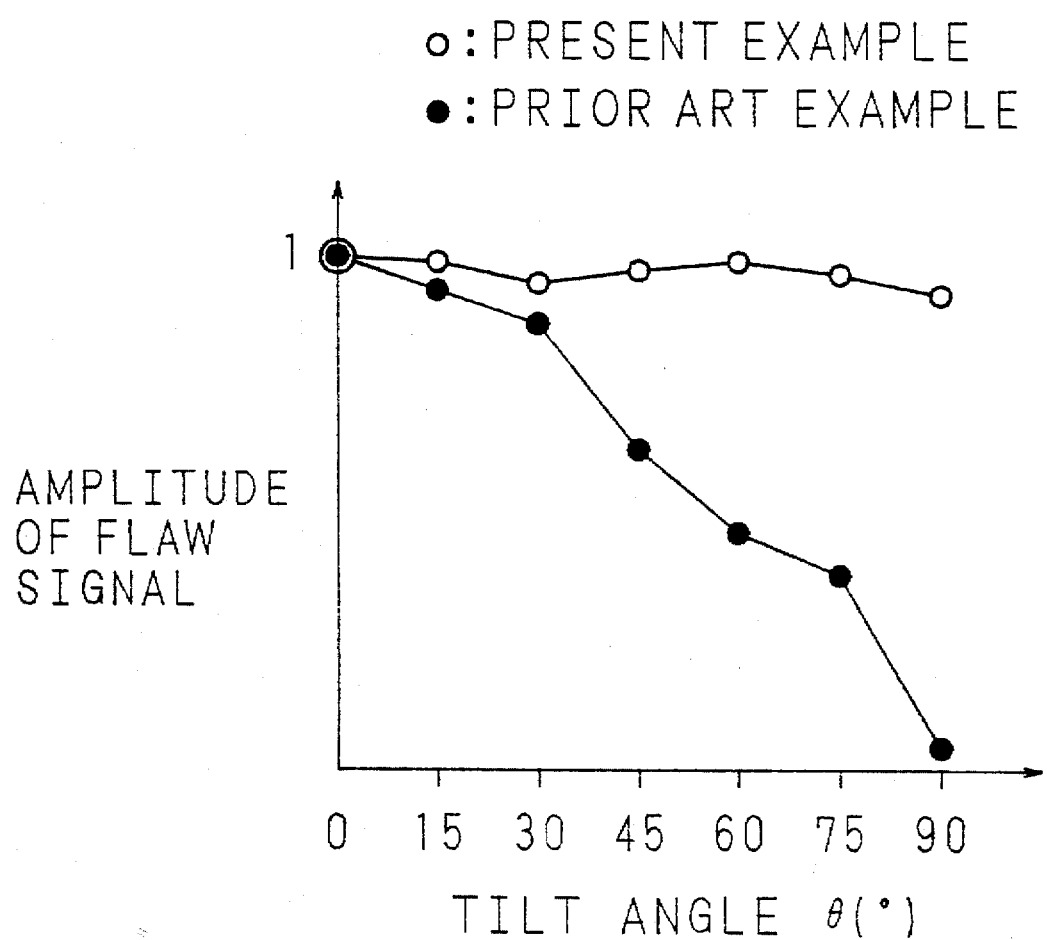
FIG. 44 is a graph showing the relation between the flaw tilt angle and the amplitude of a flaw signal.

FIG. 44 is a diagram showing the change in detection sensitivity of the leakage flux sensor according to the embodiment and the conventional leakage flux sensor for the artificial flaws K1 to K7 having a tilt angle θ with the sensor output of 1 for the tilt angle θ of 0°. As seen from FIG. 44, the flaw detection sensitivity of the conventional leakage flux sensor is sharply reduced with the increased departure of the flaw tilt angle θ away from a predicted direction (reference direction). In comparison with this, the flaw detection sensitivity of the leakage flux sensor according to this embodiment is not substantially reduced even in the case where the flaw tilt angle θ greatly departs from the reference direction, so that regardless of the flaw tilt angle θ it is seen that a flaw can be detected with a substantially constant sensitivity. Although the above-mentioned result of a test on the leakage flux sensors is based on AC excitation, a similar result of course is obtained in the case of DC excitation.

INDUSTRIAL APPLICABILITY

As described above, in a leakage flux sensor according to the present invention, a flaw occurring in an object material, in whichever direction, is detected by a sensor, and therefore DC magnetization of high flaw detection accuracy is possible without reducing the flaw detection speed. As a result, data obtained can be handled quantitatively, and the throughput of the flaw detection work is high.

In the leakage flux flaw detection apparatus according to the invention, leakage fluxes from a flaw can be increased by adjusting the direction in which an object material or a tubular material is magnetized to a frequently-occurring flaw tilt angle, and therefore a flaw can be detected with high sensitivity.

Further, the leakage flux flaw detection apparatus according to the invention can quantitatively determine the tilt angle and depth of a flaw formed in whichever direction, and thus can contribute to improvement of a manufacturing process by tracing the cause of a flaw based on the data obtained.

In a leakage flux sensor according to the invention, the large critical tilt angle of a flaw permits a flaw detection signal to be amplified to the same level as when the angle θ is 0 even for a flaw with a comparatively large tilt angle θ, thereby making it possible to avoid an erroneous decision.

Also, the leakage flux sensor according to the invention has substantially the same level of detection signals for the two flux-sensing parts regardless of the flaw tilt angle θ, thereby maintaining a high S/N ratio.

Furthermore, in the leakage flux sensor according to the invention including two concentrically-arranged sensors having a circular cross section of different sectional areas, a linear flaw can be detected always with a constant sensitivity regardless of the direction in which a flaw occurs in the case where the direction of magnetization is at right angles to the direction in which the linear flaw extends. Also, when each flux-sensing part is used in differential connection, the noise signals such as a loose material signal and a gentle change of magnetic field can be successfully suppressed.

I claim:

1. A method for flaw detection by leakage fluxes in which a tubular material is magnetized by a pair of magnetic pole units and leakage fluxes are detected by sensors interposed between said pair of magnetic pole units while searching for a flaw of the tubular material in the peripheral direction, comprising the steps of:

magnetizing the peripheral surface of the tubular material in areas by the pair of magnetic pole units in two directions, each direction being different from an axial direction of the tubular material, detecting the leakage fluxes from the tubular material by each of said sensors provided in each of the magnetization areas, and identifying a flaw of the tubular material on the basis of the detection result of leakage fluxes, wherein the step of identifying a flaw includes the steps of calculating the output ratio between said sensors, determining the tilt angle of the target flaw on the basis of a predetermined relationship between the output ratio and the flaw tilt angle on the one hand and the calculated output ratio on the other hand, correcting the amplitude of the outputs of said sensors on the basis of a predetermined relationship between the flaw tilt angle and the amplitude change rate of the sensor output signal on the one hand and the tilt angle, and calculating the depth of the target flaw on the basis of the corrected amplitude of the outputs.

2. An apparatus for flaw detection by leakage fluxes, comprising:

a pair of magnetic pole units which magnetize a tubular material in areas, sensors for detecting leakage fluxes, said sensors being interposed between said two magnetic pole units while searching for a flaw of the tubular material in an axial direction, wherein said two magnetic pole units are arranged to magnetize the peripheral surface of the tubular material in two directions, each direction being different from the axial direction of the tubular material, and each of said sensors is provided in each of the magnetization areas, and further comprising means for calculating the output ratio between said sensors, means for determining the tilt angle of the target flaw on the basis of a predetermined relationship between the output ratio and the flaw tilt angle on the one hand and the calculated output ratio on the other hand, means for correcting the amplitude of the output signals of said sensors on the basis of a predetermined relationship between the flaw tilt angle and the amplitude change rate of the sensor output signal on the one hand and the tilt angle of the target flaw determined on the other hand, and means for calculating the depth of the target flaw on the basis of the corrected amplitude of the output signals.

3. An apparatus for flaw detection by leakage fluxes, comprising:

a pair of magnetic pole units which magnetize a tubular material in areas, sensors for detecting leakage fluxes, said sensors being interposed between said two magnetic pole units while searching for a flaw of the tubular material in an axial direction, wherein said two magnetic pole units are arranged to magnetize the peripheral surface of the tubular material in two directions, each direction being different from the axial direction of the tubular material, and each of said sensors is provided in each of the magnetization areas, and wherein said pair of magnetic pole units have changeable directions of magnetization, and said sensors have changeable detection areas respectively, and further comprising means for calculating the output ratio between said sensors, means for determining the tilt angle of the target flaw on the basis of a predetermined relationship between the output ratio and the flaw tilt angle on the one hand and the calculated output ratio on the other hand, means for correcting the amplitude of the output signals of said sensors on the basis of a predetermined relationship between the flaw tilt angle and the amplitude change rate of the sensor output signal on the one hand and the tilt angle of the target flaw determined on the other hand, and means for calculating the depth of the target flaw on the basis of the corrected amplitude of the output signals.

* * * * *